(12) United States Patent
Wilson et al.

(10) Patent No.: US 8,622,929 B2
(45) Date of Patent: Jan. 7, 2014

(54) MEANS FOR SAMPLING ANIMAL BLOOD

(75) Inventors: Craig Douglas Wilson, Bondi Junction (AU); Ian Patrick Berrell, Tamarama (AU); Craig Andrew Burke, Cremorne (AU); Stephanie Norrell, Herndon, VA (US); Rita M Calnan, York, ME (US)

(73) Assignee: Noble House Group Pty. Ltd. (AU)

( * ) Notice: Subject to any disclaimer, the term of this patent is extended or adjusted under 35 U.S.C. 154(b) by 797 days.

(21) Appl. No.: 12/445,300

(22) PCT Filed: Oct. 15, 2007

(86) PCT No.: PCT/AU2007/001554
§ 371 (c)(1),
(2), (4) Date: Jul. 28, 2009

(87) PCT Pub. No.: WO2008/043156
PCT Pub. Date: Apr. 17, 2008

(65) Prior Publication Data
US 2010/0094170 A1    Apr. 15, 2010

(30) Foreign Application Priority Data

Oct. 13, 2006   (AU) .................................. 2006905688
Apr. 13, 2007   (AU) .................................. 2007901991

(51) Int. Cl.
*A61B 5/00*      (2006.01)
(52) U.S. Cl.
USPC ............................ 600/583; 600/573; 199/655

(58) Field of Classification Search
USPC .......... 119/655; 600/562, 564, 567, 570, 572, 600/573, 583, 854
See application file for complete search history.

(56) References Cited

U.S. PATENT DOCUMENTS

| | | | |
|---|---|---|---|
| 5,231,993 A | 8/1993 | Haber | |
| 6,706,159 B2* | 3/2004 | Moerman et al. | 204/403.03 |
| 2002/0130042 A1 | 9/2002 | Moerman | |
| 2003/0125668 A1* | 7/2003 | Bierman | 604/174 |
| 2004/0039303 A1 | 2/2004 | Wurster | |
| 2004/0054393 A1* | 3/2004 | Stemme et al. | 607/149 |
| 2005/0273117 A1 | 12/2005 | Teychene | |
| 2006/0036209 A1* | 2/2006 | Subramony et al. | 604/20 |

FOREIGN PATENT DOCUMENTS

DE         10315396       10/2004
WO    WO 02/085106       10/2002

* cited by examiner

*Primary Examiner* — Max Hindenburg
*Assistant Examiner* — Jonathan M Foreman
(74) *Attorney, Agent, or Firm* — Galbreath Law Offices, P.C.; John A. Galbreath

(57) ABSTRACT

A device (1410) for collecting a blood sample from an animal has a holder for holding a sampling media (1456), one or more spikes (1418) that first pass through the sampling media (1456) and penetrate into the flesh of the animal to create a puncture site to allow blood emerging from the site to be collected by the sampling media (1456) during and/or after penetration of the flesh. The device has a retainer (1427) for temporarily retaining the device (1410) on the animal whilst blood is collected and for allowing the device (1410) to be removed from the animal substantially intact for subsequent removal of the sampling media (1456) from the device.

28 Claims, 24 Drawing Sheets

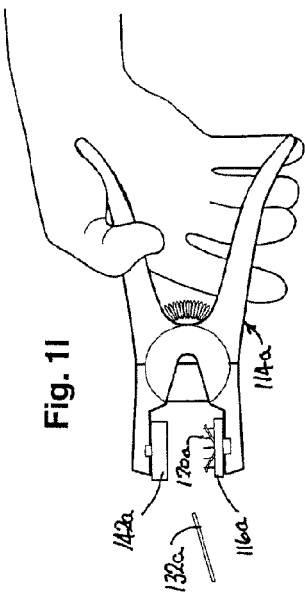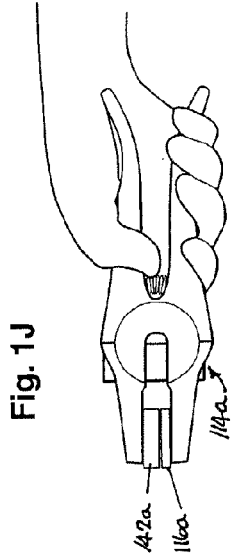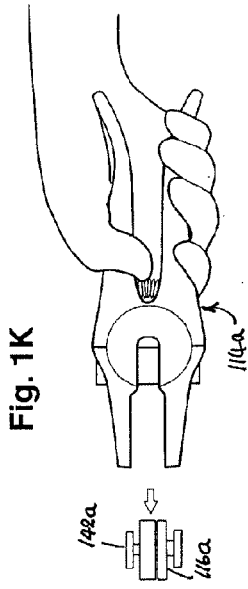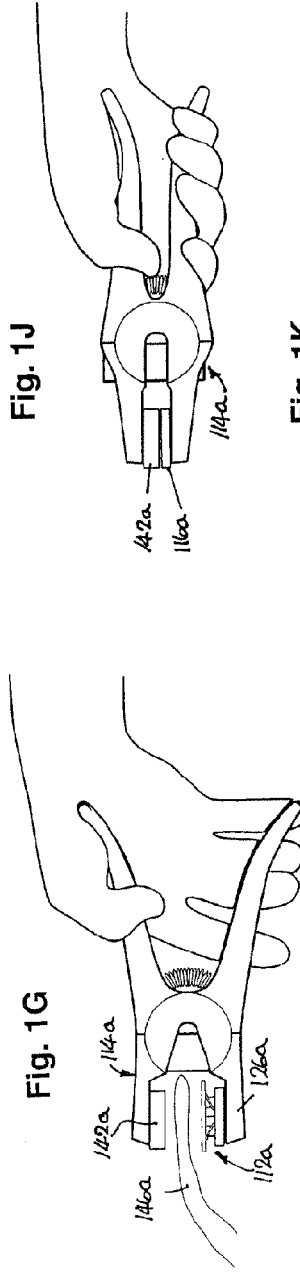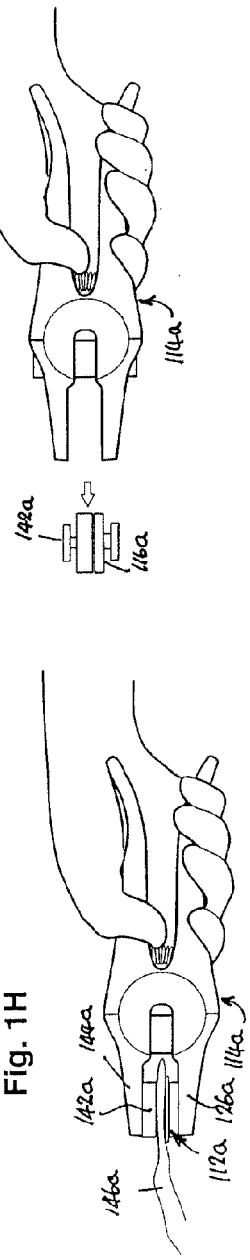

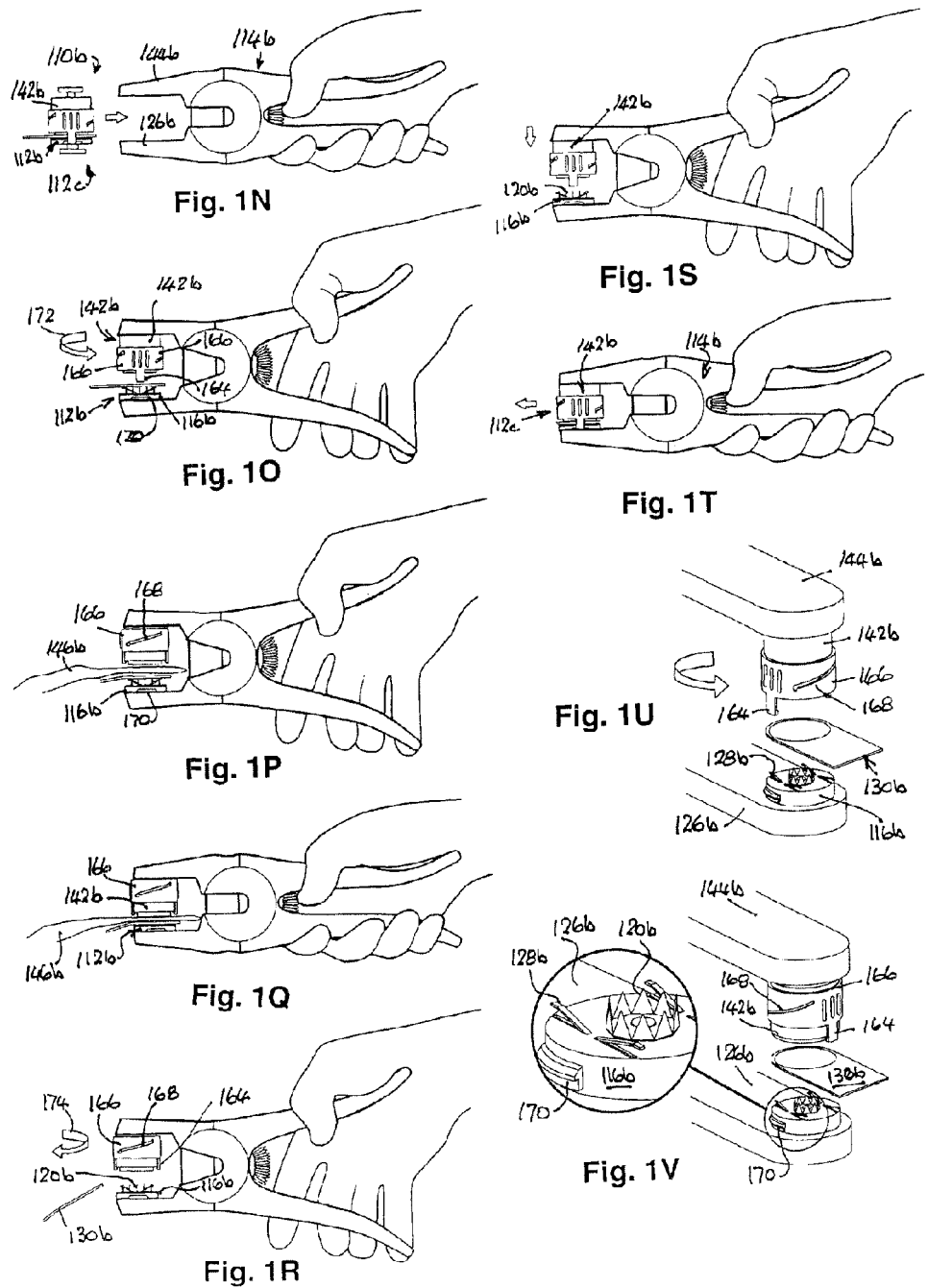

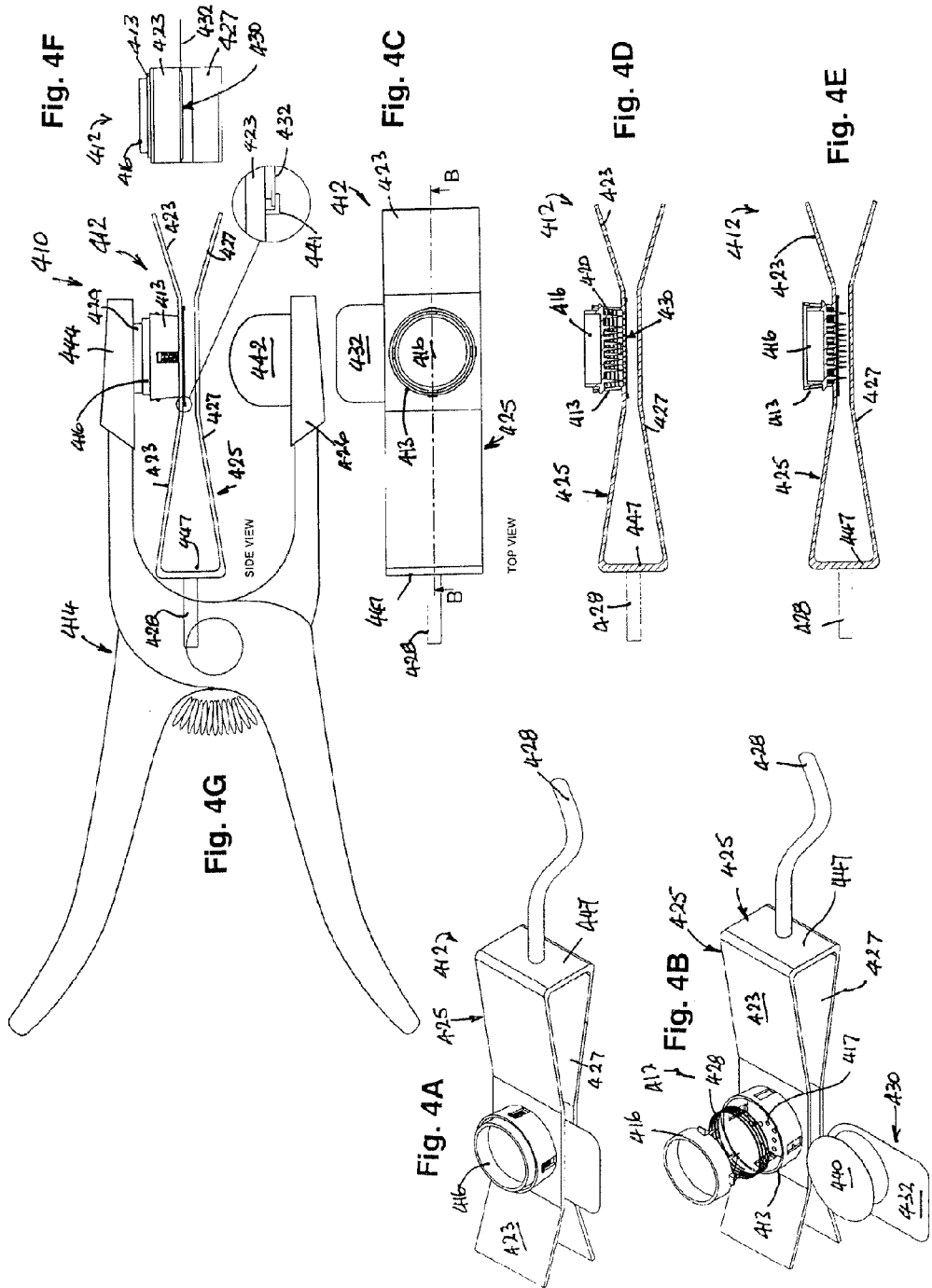

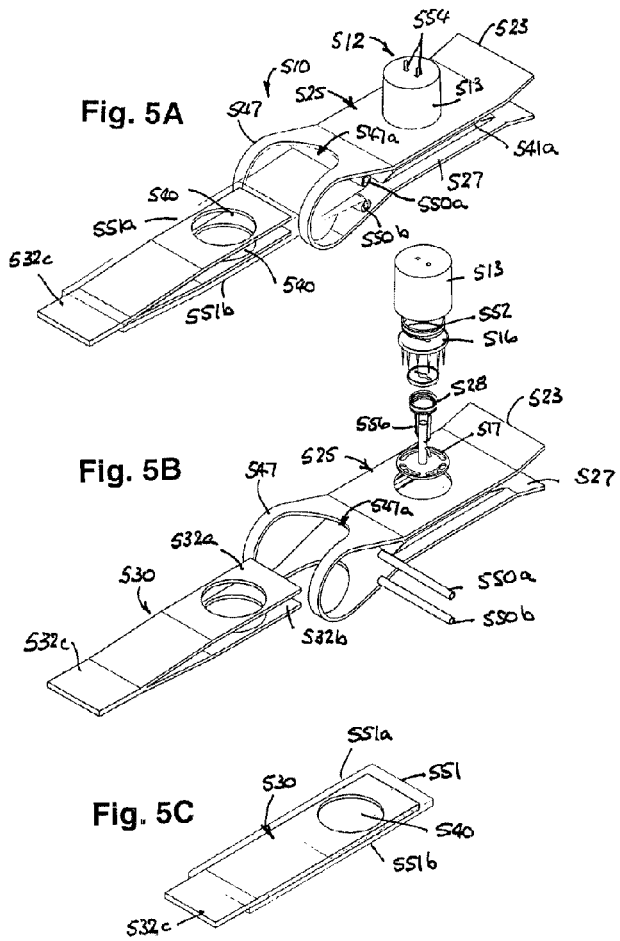
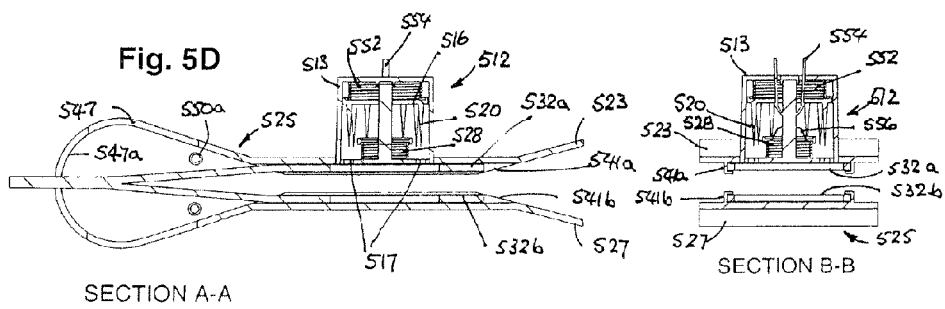
Fig. 5A
Fig. 5B
Fig. 5C
Fig. 5D
Fig. 5E
SECTION A-A
SECTION B-B

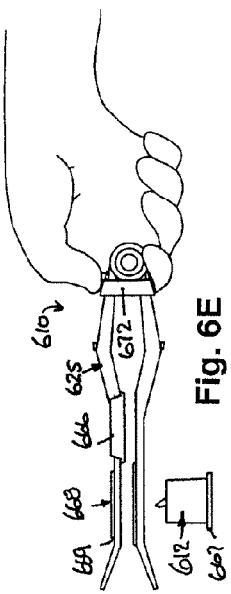
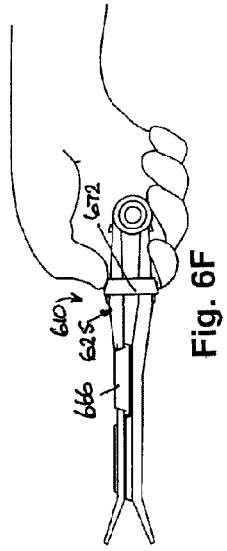
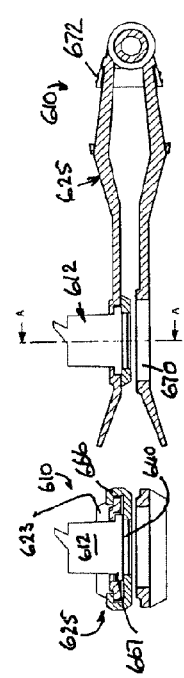
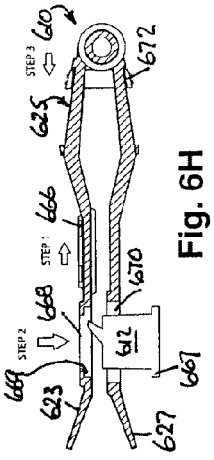
Fig. 6E   Fig. 6F   Fig. 6G   Fig. 6H
Fig. 6I
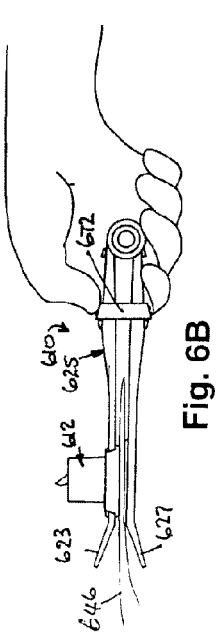
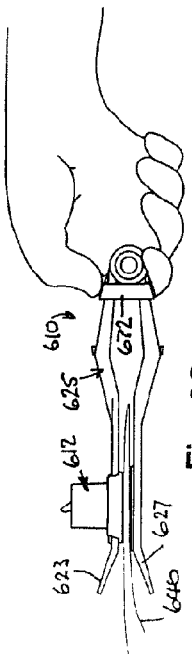
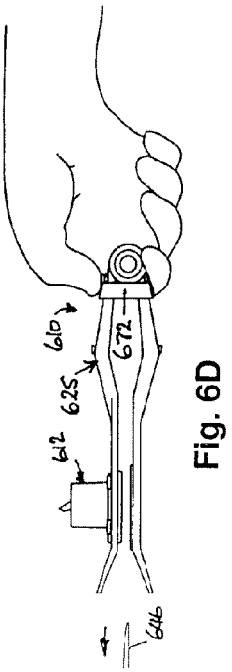
Fig. 6A   Fig. 6B   Fig. 6C   Fig. 6D

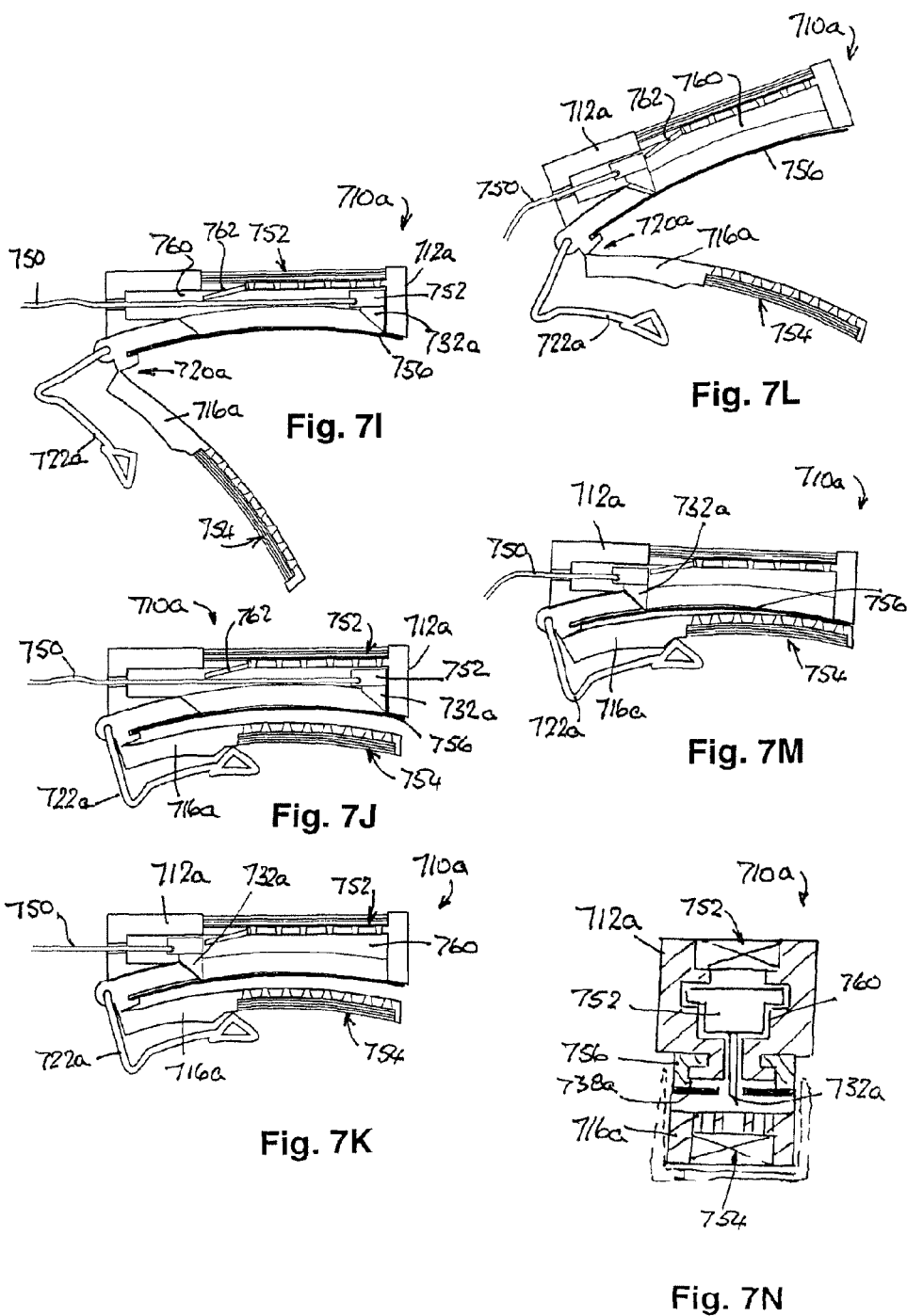

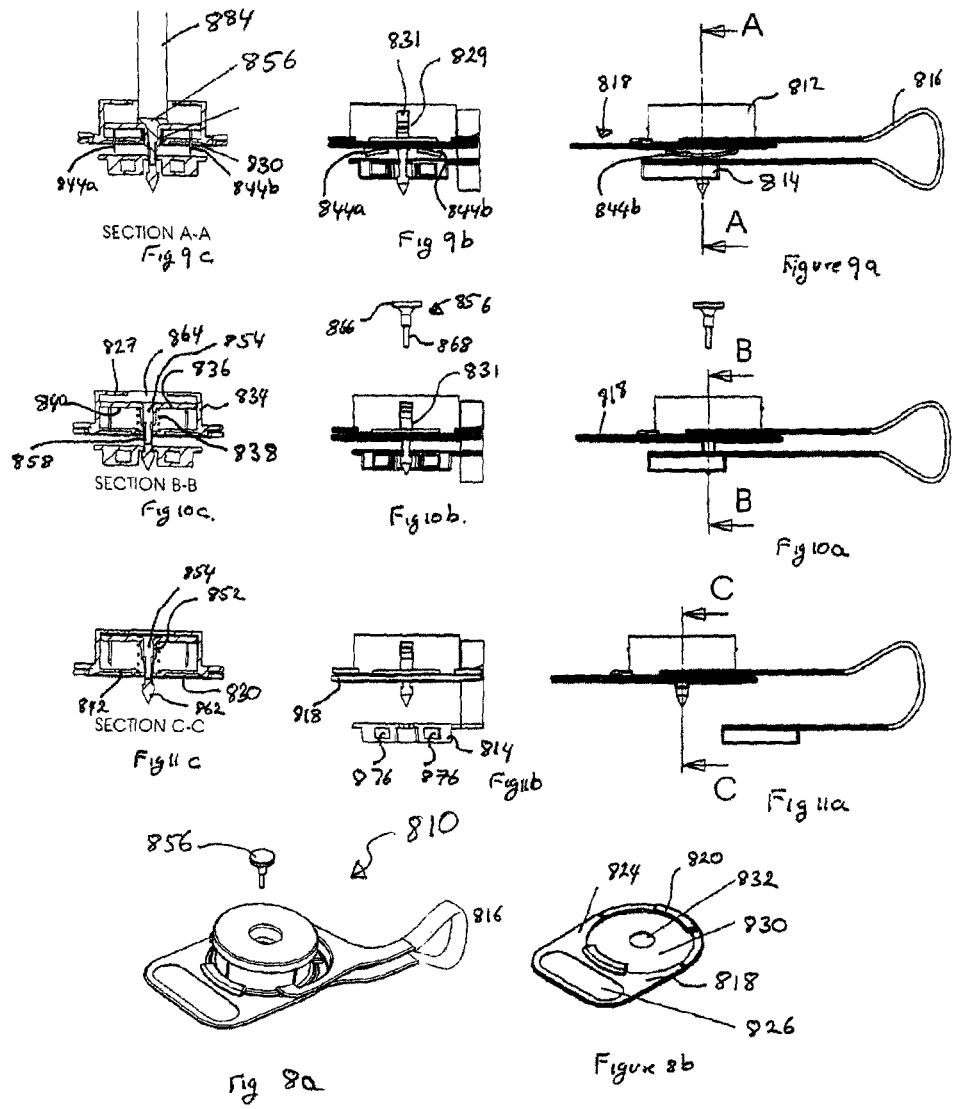

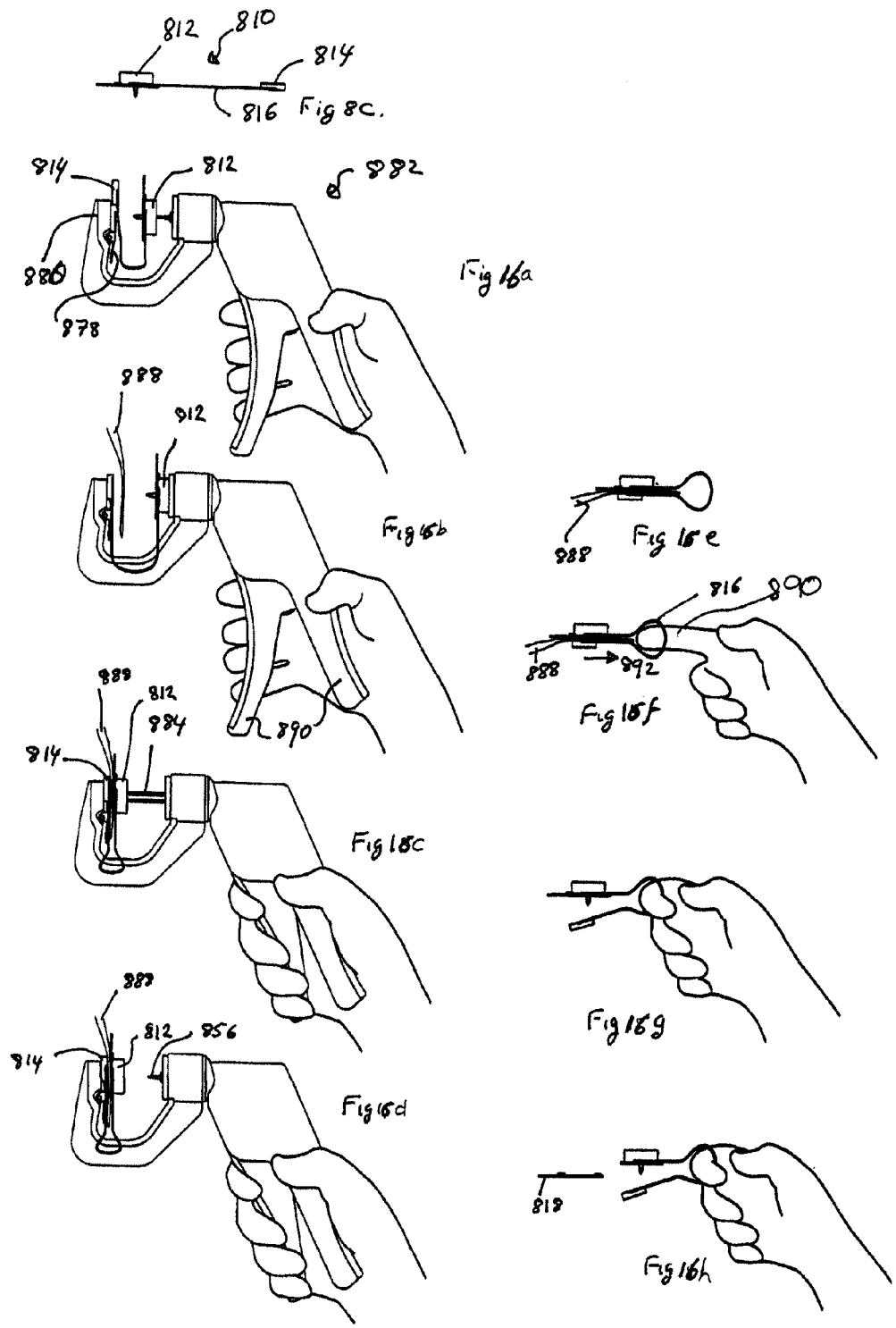

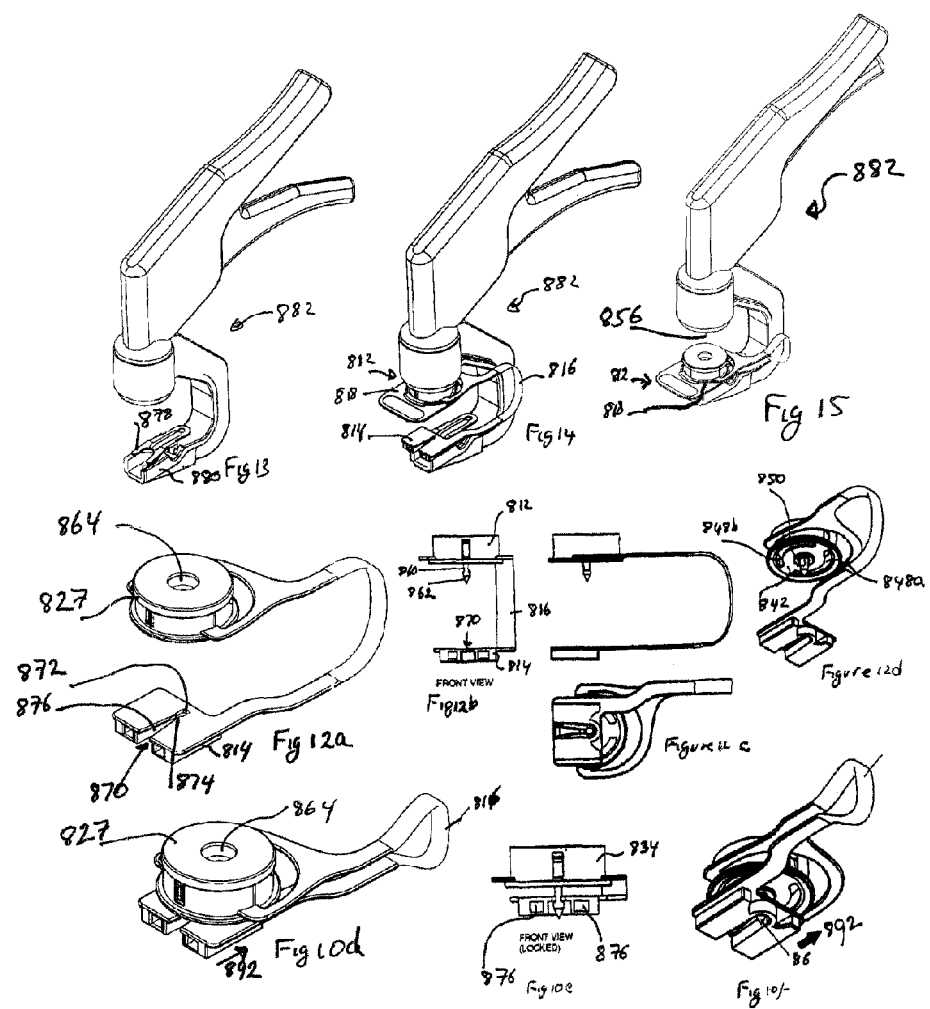

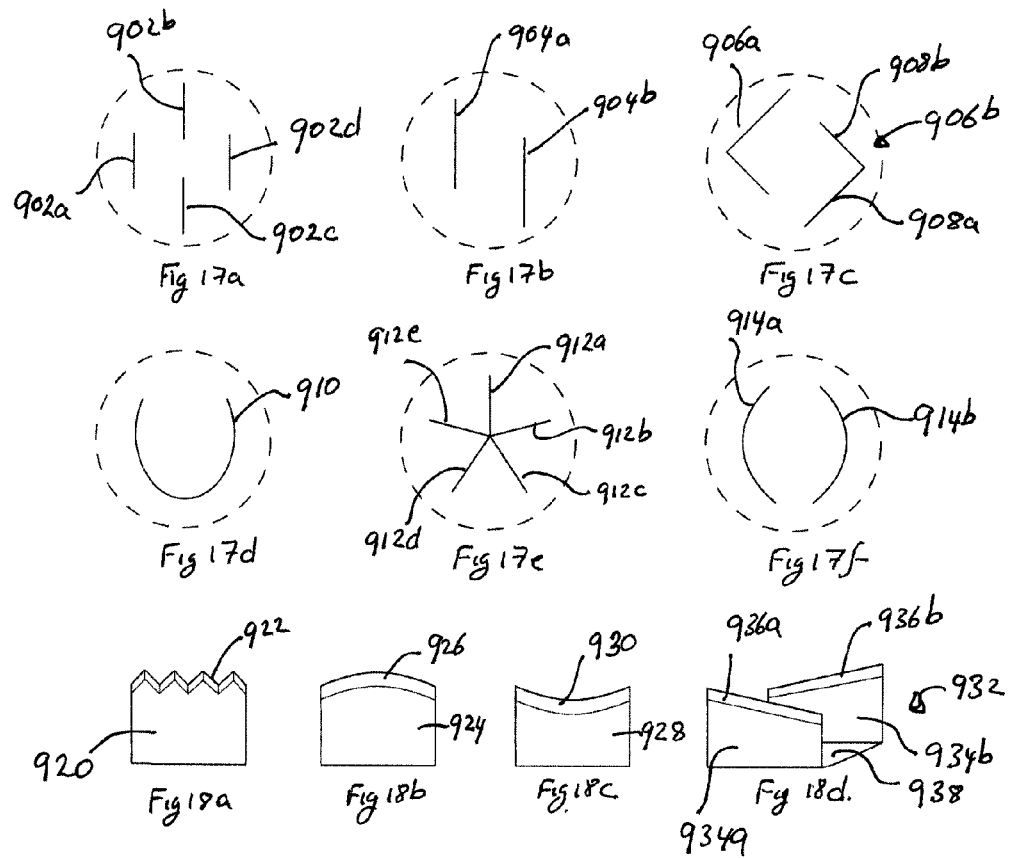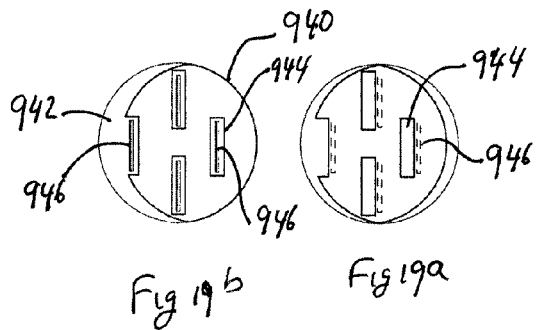

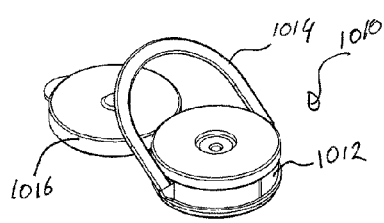
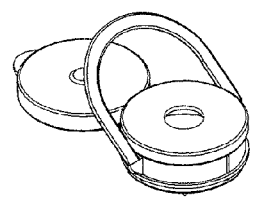
Figure 21a
Figure 22a
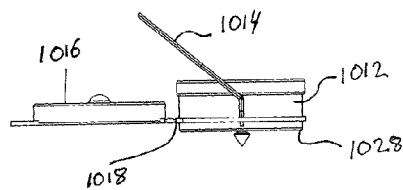
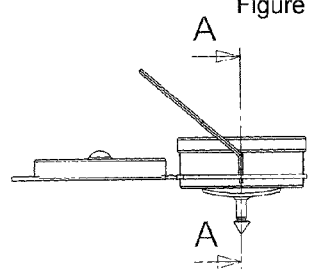
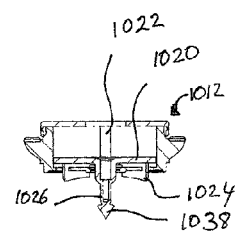
Figure 21b
Figure 22b
Figure 22d
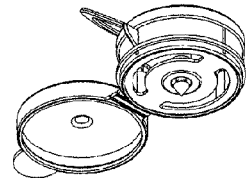
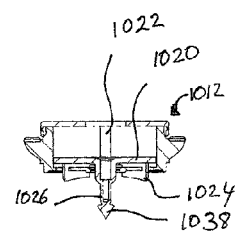
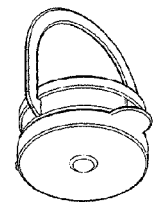
Figure 21c
Figure 22c
Figure 23

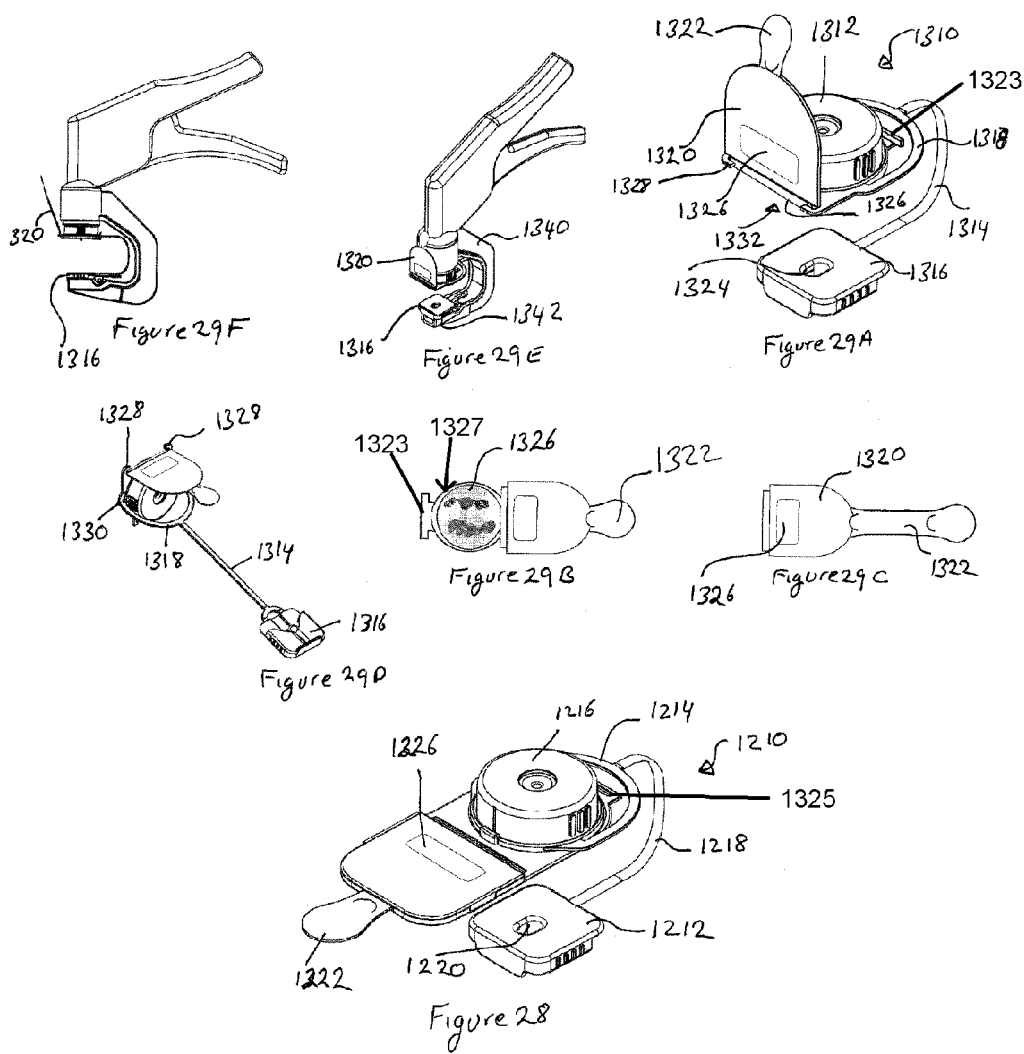

MEANS FOR SAMPLING ANIMAL BLOOD

FIELD OF THE INVENTION

This invention relates to methods and apparatus for use in obtaining samples of body fluids for later analysis. It is particularly but not exclusively concerned with the routine non-intravenous [non-IV] sampling of blood from the animals. Such samples are commonly used for DNA analysis and identification, bacteriological and viral analysis, and blood component analysis in modern animal husbandry for herd management, breeding and disease control. They are also of value in relation to public health where the tracing of stock and the identification of animal products is of increasing importance.

While, the devices and methods of the invention can be used for sampling body fluids other than blood—for example, fluids and exudates from superficial or subcutaneous infections, infestations, ulcerations and abscesses—such body fluids will normally include blood cells of the animal. For convenience, therefore, the term 'blood' will be used herein to include any body fluid that can be accessed from the surface of the skin of an animal by making cuts, punctures or other shallow penetrations of the skin. This term is not confined to whole blood.

DESCRIPTION OF RELATED ART

The growth in the routine use of animal blood analysis has created a need for methods and devices that will allow low-cost reliable collection of blood samples from large numbers of animals of many different species. Intravenous or syringe sampling from such large numbers of animals is impractical. Instead, it is common to pierce the ear or tail and to then collect the exuded blood by using blotting paper or the like.

US patent application 20050263420 A1 by Oommen discloses a device for storage, shipping and retrieval of hair follicles collected from animals for later DNA analysis. The device consists of flaps of sheet material that are secured together by adhesive so that they can be separated to expose an inner surface with light-tack adhesive adapted to receive the hair sample. After placement of the sample, the flaps can be brought together again and held closed by their adhesive. This method has the advantage that it is independent of any existing ear tag and does not require the attachment of another ear tag. However, extraction of DNA from hair follicles is more expensive and less versatile than the analysis of blood collected on adsorbent and/or absorbent material.

US patent application 2005/0051109 by Fantin et al relates to devices and methods for animal tracking based upon the collection of blood samples while attaching ear tags to animals. The ear tags have detachable sample collecting portions which have adsorbent material for collected blood from the site where the tag attachment pin is inserted or from a nearby site on the ear which is separately pierced to cause blood flow. Such a method is not suited for use on animals that already have 'standard' identification ear tags from which data has already been entered into management and tracking systems but where DNA samples have not so far been collected. There is also the problem of protecting the collected sample from contamination with other samples or with other blood associated with animal handling.

US patent application 2005/0273117 A1 by Teychene discloses the use of a detachable label with an animal ear tag, which label has a blood adsorbent material located around the area of the securing pin of the ear tag so that blood exuded after attachment of the ear tag will be adsorbed on the material and then detached from the tag with the label as a sample. This method has the disadvantages of the Fantin system mentioned above.

U.S. Pat. No. 6,509,187 to Brem discloses an ear sampler in which a portion of tissue is punched out by a male punch into a female die where it is encased. Again, the punch and die, though separately removable, are part of an ear tag and the disadvantage noted above is present. While the sample thus obtained is securely encased against subsequent contamination, it is moist and non-sterile and will be subjected to bacterial degradation during transit from farm to laboratory.

SUMMARY OF THE INVENTION

From one aspect, the invention includes a device for collecting a blood sample from an animal on sampling media placed next to the skin, the device comprising holding means for holding the sampling media for placement on the skin of an animal and spike means operable to pass through and to penetrate into the skin of the animal to create a puncture site and to then be withdrawn from the site and back through the sampling media to (i) allow blood emerging from the site to be collected by the sampling media during and/or after penetration of the skin and (ii) allow the sampling media with the blood to be removed from the device.

In another form the invention includes a device for collecting a blood sample from an animal on sampling media placed next to the animal's flesh, the device comprising:
  holding means for holding the sampling media for placement on the flesh of an animal;
  spike means operable to first pass through the sampling media and to then penetrate into the flesh of the animal to create a puncture site to allow blood emerging from the site to be collected by the sampling media during and/or after penetration of the flesh, and
  retaining means for temporarily retaining the device on the animal whilst blood is collected on the sampling media and for allowing the device to be removed from the animal substantially intact for subsequent removal of the sampling media with the blood from the device.

Preferably, the device includes guard means for guarding the spike means from contact with the fingers (or other parts) of a user before, during and/or after penetration of the animal skin.

The spike means may include one or more needle-like or lancet-type spikes of any desired cross-section that are adapted for insertion substantially perpendicular to the skin. Spikes with cruciform or star-like cross-section are suitable, as are conical spikes that are of hollow or concave form. Alternatively, the spike means may include one or more knife or scalpel-like blades adapted to form elongate cuts in the skin. The spike means may comprise an array of spikes or blades formed by plastic injection molding, by the insert molding of metal elements into a plastic platen, by metal die-casting or by stamping, folding, or upsetting of sheet metal by techniques known in the art.

The sampling media may be any suitable natural or synthetic material or combination of materials known in the art for collecting fluid, blood, cells, proteins or related materials. As such the sampling media may be fibrous, foamed, film-like or of another construction. The sampling media may have hydrophilic or hydrophobic properties (or both), but we have found thin sheet fibrous sheet material, such as paper, to be convenient. The sampling media may be absorbent, adsorbent or both absorbent and adsorbent. The media may be a single layer of material or may be multi-layered. Where the sampling media is multi-layered, each layer may be formed of different materials and/or materials having different properties. However, the specific construction of the sampling media is not critical to the invention.

It is desirable to pre-puncture or pre-slot the material of the sampling media to minimize tearing or ripping as the spike means passes there-through. The holding means can take a variety of forms. It may include a carrier, frame, card or other support having a window of sampling media. This is suitable where the sampling media is thin, fragile or delicate, as the carrier or the like can then be used to position the sampling media during use of the device, to remove the sample from the device and to assist packaging and transportation of the sample. The carrier may also include identifying information such as a barcode, an RFID device, and an area for handwriting.

The device may have a body within or on which the spike means is located and the holding means can serve to removably attach the sampling media to the body so that it is juxtaposed with the spike means to allow appropriate insertion and withdrawal of the spike means there-through. Where the sampling media material is sheet material, the holding means may comprise slots, brackets or the like formed within the body and adapted to hold the sheet material in position. Alternatively, the holding means can be an adhesive by which the material is held in place relative to the body. Indeed, such slots or adhesive can also be employed to position a carrier or the like relative to the body, where the carrier is used to mount or hold the sampling media as previously indicated.

The body of the device can have a face against or near which the material is held and through which face the spike means can be extended and withdrawn enroute to and from the site via the sampling media. The face can be used to position the material closely adjacent the site to facilitate blood collection.

Clamp and/or retaining means may be provided by which the face of the body can be pressed against the site with the material (and/or the holding means for the material) located between the face and the site, so that the sampling media is positioned closely adjacent the site to facilitate blood collection. The clamp means can be integrated with the device, form a detachable part of the device, or the device can be separate and independent of the clamp means. For example, the clamp means can be a clamping tool—such as a pliers-like clamp—and the device may be loaded into the tool and removed from it as a cartridge.

The clamp means may be employed to press the spike means into the skin of the animal and to effect the withdrawal of the spike means. Alternatively, the clamp means may be used to position and hold the device in place while the spike means is activated independently. We have found it preferable for the device to include light-weight clamp means by which the device can be left attached to the ear of an animal without support to provide sufficient time for blood to be exuded from the site and collected by the sampling media. This will generally be between a few seconds and nearly a minute, depending upon the animal, the sampling site and the type of spike means used.

When used for collecting blood from a flap of skin, such as an animal's ear, the device may include a pin or the like having a head that is driven through the ear and preferably into a retainer located on the opposite side of the ear. After the device has been attached to the animal's ear for sufficient time the retainer and pin are separated. The pin preferably has an arrow shaped head that is retained by a slot or aperture in the retainer. The pin may be released from the retainer by movement along the slot or aperture. Preferably the slot or aperture has a necked portion that inhibits movement of the pin along the slot or aperture. In another form the pin head may be detached from the shank of the pin, so releasing the device. This may be by rotating the pin head relative to the shank so as to break the pin or by cutting the pin head from the shank.

An auto-retracting ear-tagging type gun/clamp or manual ear tagging type of pliers may be used to drive the pin through the ear into the retainer (located on the opposed jaw) and the spike means into the animal's ear. With auto-retracting ear-tagging guns the user merely squeezes a pair of handles together in a single action and this causes a plunger to extend and then retract. Use of an auto-retracting ear-tagging gun allows the user to attach the device of the invention to the ear and have the plunger released from the body of the device in a single action, in a similar manner to attachment of an ear tag. Because the pin is secured to the retainer the gun can then be easily removed from the retainer by a sliding action.

If desired, the pin and spike means may be located in a housing that may be detached from the sampling media and the remainder of the device. This allows the pin and spike means may be disposed of separately.

In an alternative embodiment the retainer may be omitted and the pin may be driven through the ear and the device retained on the ear by the head of the pin.

The sampling media may be movable between an operative position in which it underlies the spike means and a storage position in which it is remote from the spike means. Preferably, housing is provided into which the sampling media is located when in the storage position. The housing may be detachable from the remainder of the device.

The guard means can take a variety of forms. In one form it may comprise the above-mentioned body of the device from which the spike means is extended and into which it is withdrawn so that, both before and after use of the spike means, the body serves to guard the spike means against contact by the user. In another form, the guard means may comprise a press-pad mounted in opposition to the spike means so that an ear, tail or skin fold of an animal can be clamped or positioned there-between and so that, after a sample has been taken and the site released, the spike means can be driven into or onto the press-pad, or the press-pad and the spike means can be locked together, to guard the spike means from contact. These options are of value where a clamp tool is used and the spike means is mounted on one jaw and the press-pad is mounted on the opposing jaw of the tool.

Thus, from another aspect, the invention comprises a method of collecting blood from sample site on an animal including the steps of holding blood collecting sampling media adjacent the site, driving spike means through the sampling media into the site and withdrawing the spike means from the site and back through the sampling media so that blood exuded from the sample site is collected by the sampling media while the spike means is in the site and/or after the spike means has been withdrawn from the site.

The method may include the step of guarding the spike means against contact with the fingers of the user after withdrawal of the spike means from the site. This may be done by extending the spike means from within the body of a device and/or by withdrawing the spike means into the body. It may also or alternatively be done by pressing the spike means into, or attaching it to a press-pad or the like after withdrawing it from the site. The method may include supplying the press-pad and the spike means as a coupled unit (which thereby guards the spike means against contact before use) or coupling the spike means with the press-pad after use, thereby guarding the used spike means from user contact.

The method preferably includes the step of removing the sampling media after the spike means has been withdrawn there-through, the removed material with the collected blood preferably being packaged or covered against contamination as it is removed from the device or there-after.

The method may include the step of clamping the device to the animal and, in so doing, driving the spike means into the site. It may also include the step of releasing the device from the animal and, in so doing, withdrawing the spike means from the site. On the other hand, the method may include the step of attaching the device to the site, activating the spike means to penetrate and withdraw from the site and then leaving the device attached to the site for sufficient time to permit blood exuded from the site to be collected by adsorption onto and/or absorption into the sampling media. Indeed, aspects of these methods may be combined by using a clamp to hold the device to the site to effect penetration of the spike means, releasing the clamp to effect the withdrawal of the spike means from the site, removing the clamp and then leaving the device attached to the site for sufficient time to permit blood exuded from the site to be collected.

From another aspect, the method may include the step of attaching a sampling device to a sample site, such as an ear, activating the (preferably automatic) penetration and withdrawal of spike means into and from the site through blood collecting sampling media placed on or adjacent to the site, leaving the device attached to the site for sufficient time to permit blood exuded from the site to be collected and then removing the device and the sampling media from the site.

The method may include the step of driving or forcing the spike means into the site substantially orthogonally to the skin and removing the spike means in substantially the same manner. In addition or alternatively, a linear motion may be applied to the spike means so that the skin is cut linearly as well as orthogonally. The spike means may be driven into the site by spring means and/or withdrawn from the site by spring means. Alternatively, the spike means may be driven into the site and/or withdrawn by manual means such as a hand-operated clamp, lever or a draw-string.

In one embodiment, the spike means can be mounted on or include a movable platen within the body of the device so the movement of the platen to effect withdrawal of the spike means causes reduced air pressure on the body side of the sampling media thereby assisting exudation of blood from the site onto the material. In one convenient form, annual rubber-like spring means may be located between the face of the body that is adjacent the material and the spike means may include spikes that can be extended through holes in the face by compressing the spring means. Withdrawal of the spikes thereby permits the rubber-like spring means to expand and, in so doing, to generate the reduced air pressure (exerted through the holes in the face of the body on the material).

From another aspect, the invention may include the steps of mounting the spike means and blood collecting sampling media on one jaw of a clamp, mounting a press-pad on the other (and opposed) jaw of the clamp, bringing the jaws of the clamp together about the ear of an animal to cause the spike means to penetrate the ear and to allow exuded blood to be collected by the sampling media, releasing the clamp to withdraw the spike means and to release the ear, and removing the sampling media with the collected blood sample. Additional steps may also be employed, such as re-closing the clamp (without the ear in place) to couple the press pad with the spike means and to thereby protect the spike means against injurious contact with the user, and removing the coupled spike means and press-pad from the clamp as a unit. Indeed, prior to the use of the clamp, additional steps may be employed of mounting a coupled press-pad and spike means onto the jaws of the clamp and opening the jaws of the clamp to separate the press-pad and spike means ready for use.

The method may include the step of leaving the sampling media with the blood sample within or on the device and forwarding the device or a portion thereof to a laboratory for separation and analysis. In one embodiment where the device includes attachment or clamp means whereby the device can be attached to an ear (or the like) while the sample is being collected and then released, the step of re-closing the attachment or clamp means to cover or enclose the sampling media within the device may be employed.

From another aspect the method may comprise the step of creating a partial vacuum or a low-pressure on the device side of the sampling media so as to aid the exudation of blood from the site onto the sampling media.

In one embodiment, the spike means may comprise a platen bearing at least one spike, lancet or knife that is located within a body and is moveable to expose the spike or the like from a face of the body for penetration into the animal. The sample collecting means, which may conveniently be a sheet of sampling media, can be attached to the face of the body so that the spike or the like passes there-through into the animal and so that blood emerging from the wound is collected by the sampling media. Spring means may be provided to effect or aid withdrawal of the spike or the like back into the body, after it has penetrated the animal.

In another embodiment, the spike means may comprise at least one lancet or knife within the cartridge that is adapted to be drawn across the skin of the animal so that the wound consists of one or more linear cuts. In that case, the lancet or knife passes through the sample collecting means and is preferably returned to a guarded position within the cartridge, as in the case of the spikes or the like. The knife or lancet (as with the spikes) may be spring-driven or manually driven to effect insertion and/or withdrawal.

In another broad form the invention also provides a device for sampling media, including:
  a hollow housing having a first opening therein;
  sampling media assembly slidably received within the housing through the first opening and movable between and operative position and a storage position,
  wherein,
    in the storage position a sampling area of the sampling media assembly is located within the housing, and
    in the operative position the sampling area is located outside of the housing.

The sampling media assembly may comprise sampling media located on or attached to a carrier that is received within the housing. Alternatively the sampling media assembly may comprise sampling media without a carrier.

Preferably the sampling media assembly includes one or more handles or extensions that extend out of second opening (s) in the housing, whereby the sampling media assembly may be moved between the operative and storage positions. Preferably the handle or extension extends through a second opening opposite the first opening. However, the handle(s) may be located on one or both sides of the sampling media assembly.

Preferably the sampling area is located at one end of the sampling media assembly and the handle is located at an opposite end thereof.

The device preferably includes locking means to lock the sampling media assembly in the storage position when the sampling media assembly is moved from the operative position to the storage position. Preferably the locking means comprises one or more barbs on the handle that pass through the second opening and engage the outer surface of the housing adjacent the second opening.

The housing may be formed of cardboard or paper of other suitable sheet-like materials, such as plastics or foil materials. Alternatively the housing may be substantially rigid.

The housing may be attached to a sampling device with which the sampling media is used.

The housing may be formed integrally with at least part of a sampling device with which the sampling media is used. When formed integrally with the sampling device the housing may be defined at least partially by a line of weakness, whereby the housing may be removed from the device after use.

BRIEF DESCRIPTION OF \ THE DRAWING(S)

Having broadly portrayed the nature of the present invention, examples will now be described with reference to the accompanying drawings, in which:

FIGS. 1F-1M depict a first variation of the first example,

FIGS. 1N-1V depict a second variant of the first example.

FIGS. 4A-4G depict the device of the fourth example of the invention.

FIGS. 5A-5I depict the device of the fifth example of the invention.

FIGS. 6A-6I depict the device of the sixth example of the invention

FIGS. 7I-7N depict a variation of the device of the seventh example.

FIGS. 8A and 8B depict the device of the eighth example of the invention,

FIGS. 9a to 9c depict the device of the eighth example being attached to an animal's ear. For clarity the ear is not shown.

FIGS. 10a to 10f depict the device of the eighth example whilst attached to an animal's ear. For clarity the ear is not shown.

FIGS. 11a to 11c depict the device of the eighth example after it has been removed from an animal's ear.

FIGS. 12a to 12d depict the device of the eighth example before use.

FIG. 13 shows an ear tagging gun with which the eighth example may be used.

FIG. 14 depicts the eighth example attached to an ear tagging gun before use.

FIG. 15 depicts the eighth example attached to an ear tagging gun after being attached to an animal's ear.

FIGS. 16a to 16h depict the steps of use of the device of the eighth example.

FIGS. 17a to 17f depict plan views from below of variations of blade arrangements for use with the eighth example.

FIGS. 18a to 18d depict side views variations of blade shapes for use with the eighth example.

FIGS. 19a and 19b show a shutter arrangement for use with the blade arrangement of FIG. 17a.

FIGS. 21a, 21b and 21c are, respectively, a perspective view from above, a side view and a perspective view from below of the tenth example in an initial state.

FIGS. 22a, 22b, 22c and 22d are, respectively, a perspective view from above, a side view, a perspective view from below and a cross sectional view of the tenth example in an extended state.

FIG. 23 is a perspective view from below of the tenth example in the closed state.

FIG. 28 is a perspective view from above of the twelfth example in the retracted state.

FIG. 29a is a perspective view from above the thirteenth example in an initial state.

FIG. 29b is a plan view from below of the sampling media assembly and housing of the thirteenth example after removal from an animal's ear prior to retraction of the sampling media into the housing.

FIG. 29c is a plan view from below of the thirteenth example after removal of the sampling media from the rest of the device and after retracting into a protective housing.

FIG. 29d is a perspective view from above of the thirteenth example as it is being removed from an animal's ear. For clarity the ear and user are not shown.

FIGS. 29e and 29f are, respectively, a perspective view from above and a side view of the thirteenth example mounted on an ear tagging gun prior to use.

DETAILED DESCRIPTION OF THE EXAMPLES OF THE INVENTION

Example 1

Figure 1A:
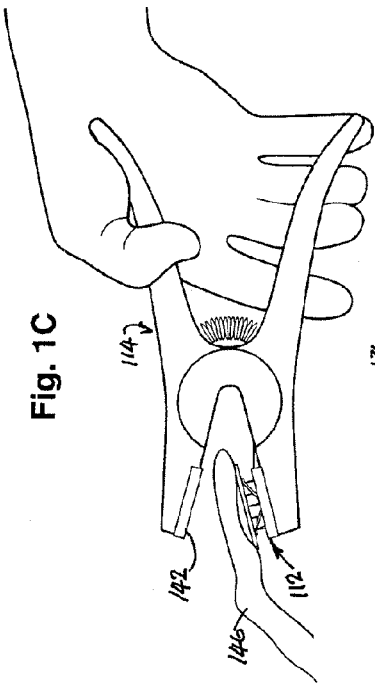
FIGS. 1A-1E depict the device of the first example of the invention.
Figure 1B:
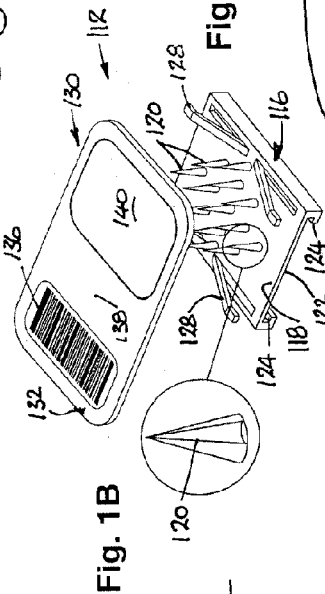
Figure 1D:
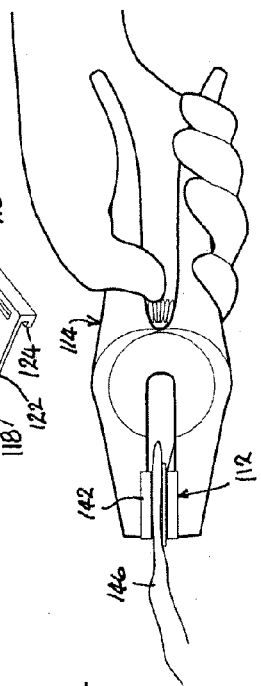
Figure 1C:
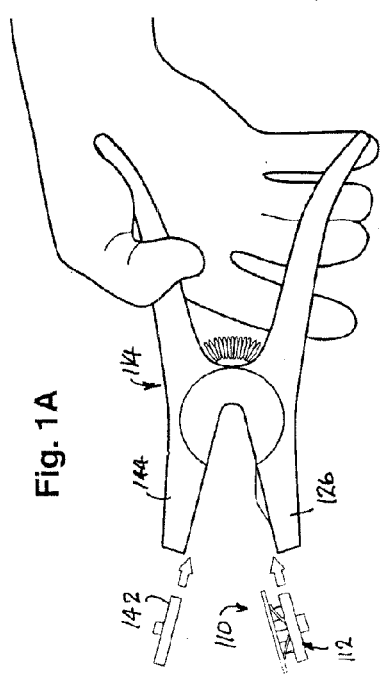
Figure 1E:
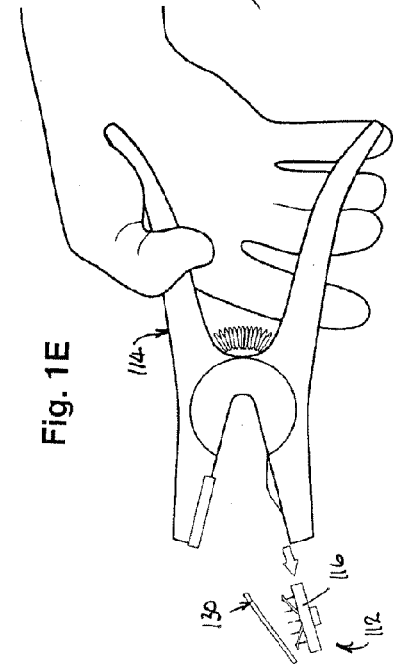

The first example of a device and method of the invention will be described with reference to FIGS. 1A to 1E with a first variant described with reference to FIGS. 1F-1M and a second variant described with reference to FIGS. 1N-1R.

In this example, the device 110 of the first example (see particularly FIGS. 1A and 1B) is a replaceable sample-collecting cartridge 112 (shown in exploded form in FIG. 1B) that is loaded into a pliers-like clamp tool 114, cartridge 112 comprising a platen 116 having an inner face 118 from which a plurality of needle-like or lancet-like spikes 120 project and an outer face 122 that has grooves 124 by which platen 116 (and therefore cartridge 112) can be slid onto and detachably retained by the lower jaw 126 of clamp 114, which is grooved longitudinally in a complementary fashion (not shown). Leaf-springs 128 are attached to the sides of platen 114 on inner face 118 thereof so as to support a sample carrier 130 above spikes 120, carrier 130 preferably being attached to the tops of leaf-springs 128 so that platen 114, spikes 120, springs 128 and carrier 130 form an assembly that comprises cartridge 112. [Note that cartridge 112 is shown exploded for clarity in FIG. 1B.] In this example, sample carrier 130 includes a card 132 bearing a barcode 136 and written identification 138 and, preferably, providing space on which the user can write. Most importantly, card 130 includes a window area that is covered with sheet like sampling media 140 which is arranged opposite spikes 120.

In this example, an independently replaceable press-pad 142 can be separately fitted to the upper jaw 144 of clamp 114 and is molded from plastic material that is sufficiently soft to allow the points of spikes 120 to penetrate without being bent over or distorted.

The operation of device 110 of the first example and the method of sample collection will now be described with reference to FIGS. 1A-1E. Cartridge 112 and press-pad 142 are separately loaded onto lower and upper jaws 126 and 144 (respectively) in the manner indicated above. The open clamp 114 is then placed around the animal's ear 146 [FIG. 1C] and forcibly closed thereon [FIG. 1D] to compress springs 128 and force spikes 120 through sampling media 140 and into the selected sample site on the ear 146. Clamp 114 is held closed for a few seconds to allow blood from the site to ooze out into contact with sampling media 140. After which, clamp 114 is released and opened to free ear 146, allowing sample carrier 130 to be detached from springs 128 and slipped into a suitable individual package (not shown). Spike cartridge 112 (minus carrier 130) is then removed from lower jaw 126 of clamp 114 and discarded into a sharps-bin.

If spikes 120 are deemed too short to go right through the ears (146) of the type of animal from which blood is being sampled, press-pad 142 can be retained on upper jaw 144 of clamp 114, unless it is clearly soiled, in which case it should be replaced. On the other hand, if spikes 120 are likely to go right through the ears of the animals involved, press-pad 142 should be replaced after each use. In either case, clamp 114 is readied for re-use by loading another cartridge-like device onto lower jaw 126 of clamp 114.

It will be seen from the above description that the holding means, whereby the sampling media 140 is positioned and held against the sample site, is carrier 130 and leaf springs 128 by which it is attached to platen 116 that may be said to form the body of the device. Of course, the combination of these components (with the spikes 120) together forms the cartridge-like device 112.

A disadvantage of device 110 is that it is possible for the user's fingers to be pierced by contaminated spikes 120 when cartridge 112 is being removed and transferred for disposal. FIGS. 1F-1V illustrate two variants of the device of the first example that eliminate this problem by fixing cartridge 112 to press pad 142 before the cartridge is removed. For this purpose it will be convenient to use a parallel-jaw pliers-like clamp. The first variant will be described with reference to FIGS. 1L and 1M and the second will be described with reference to FIGS. 1N to 1V. The same reference numerals will be used for parts corresponding with those described with reference to FIGS. 1A-1E except that the suffix 'a' will be added for the first variant and the suffix 'b' will be added for the second variant.

The parallel-jaw pliers-like clamp use for the variants is indicated at 114a. In the first variant, sample collecting cartridge 112a and press-pad 142a are separately loaded onto the lower and upper jaws 126a and 144a (respectively) of clamp 114a. In the second variant, sample collecting cartridge 112b and press-pad 144b are supplied as a single integrated cartridge 112c that is fitted to and removed from clamp 114a as a unitary assembly.

The general mode of operation of device 110a that forms the first variant of the first example is indicated in FIGS. 1F-1K, which are substantially self-explanatory:

Cartridge 112a and press-pad 114a are loaded into jaws 126a and 144a (FIG. 1F),

An ear 146a is then placed between the jaws of clamp 114a (FIG. 1G) which are then closed on the ear (FIG. 1H), Clamp 114a is opened to release the ear and allow removal of sample carrier card 132a, Clamp 114a is the re-closed to lock cartridge platen 116a and press pad together (FIG. 1J), and Pressure on clamp 114a is relaxed to allow cartridge 112a and press-pad 142a to be removed as an assembly for disposal.

Optionally, carrier 132a can be left in place between cartridge 112a and press pad 142a and the entire cartridge/press pad unit sent to the analytical laboratory where the unit is separated and carrier 132a is extracted.

Figure 1L:
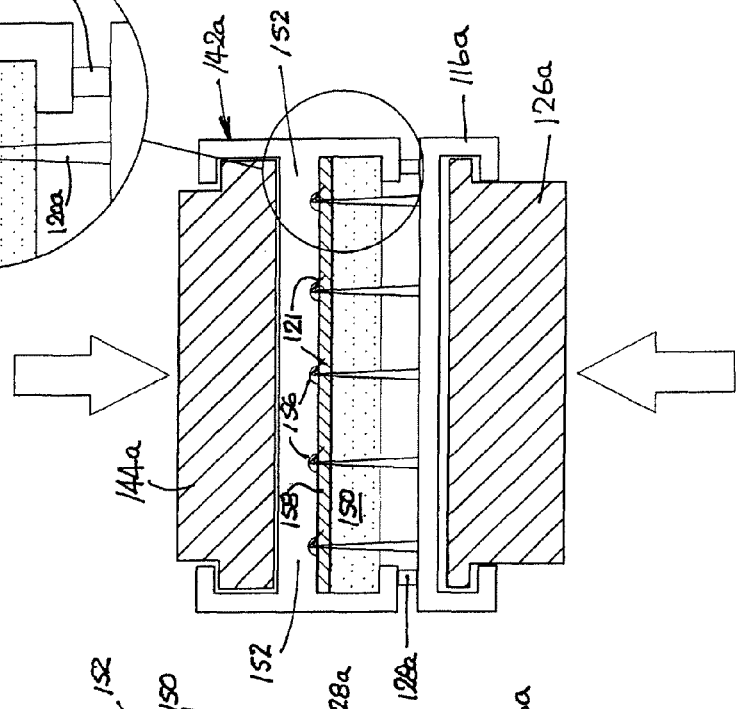
Figure 1M:
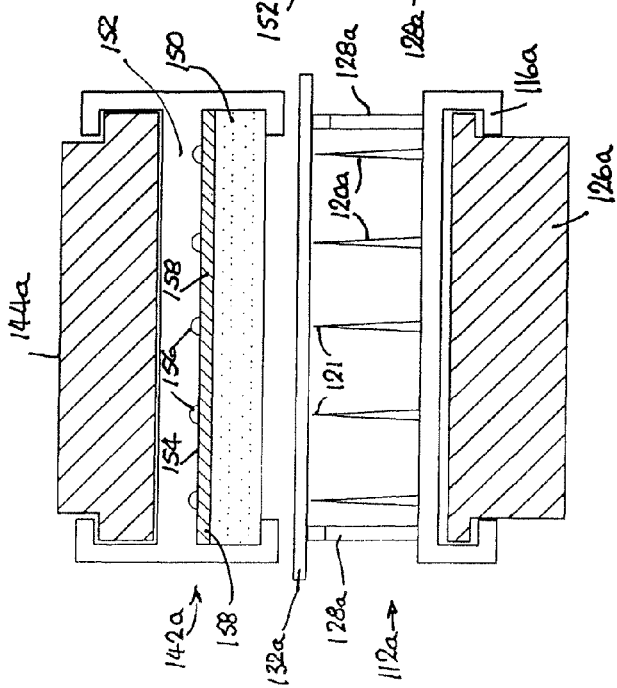

As shown in the detailed cross-sections of FIGS. 1L and 1M, the cartridge 112a of device 110a has spikes 120a on platen 116 formed from a material (plastic or metal) that allows their tips 121 to be permanently bent over when pressed against a hard object. No other modification of spike cartridge 112 is needed. However, a modified press-pad 142a is employed, which differs from pad 142 in that it is has a relatively thin and penetrable soft face 150 backed by a relatively hard body 152. If desired, the inner face 154 of body 152 can be provided with indentations or dished recesses 156 opposite spikes 120a shaped so as to assist in turning their tips 121 upon forcible contact. A further option is to mould a thin layer of fabric 158 between face 154 of body 152 and face pad 150 so that, while penetration of tips 121 is not significantly inhibited, their withdrawal after being turned or bent will be difficult. The manner of operation is shown in the section drawing of FIG. 1M that depicts spikes 120a in forcible contact with body 152 of modified press-pad 142 with their tips 121 turned so as to inhibit separation of platen 118a from modified press pad 142a.

It will be appreciated that press-pad 142a of the above described variant of the first example can be regarded as the aforementioned guard means.

In the second variant of the first example, shown in FIGS. 1N-1V, device 110b is an integrated cartridge 112c which incorporates sample collecting cartridge 112b and press-pad cartridge 142b, integrated cartridge 112c being loaded into and removed from lower and upper jaws (126b and 144b) as a unit. Press pad 142b is attached to sample collecting cartridge 112b by hooks 164 that depend from a rotatable sleeve 166 which has helical slots 168 that engage pins (not shown) protruding laterally from press pad 142b. [See detail of FIGS. 1U and 1V] Thus rotation of sleeve 166 in one direction will raise it (and its dependent hooks 164) relative to press pad 142b and lower it when rotated in the opposite direction.

As supplied, integrated cartridge 112c is formed by engagement of hooks 164 with shoulders 170 (see detail of FIG. 1V) formed on platen 116b of sample collecting cartridge 112b, and it is loaded into clamp 114b with the jaws at or near their closed position. (FIG. 1N). After loading, clamp 114b is opened forcing the release of hooks 164 (which have lateral flexibility) from shoulders 170, the resulting position then being shown by FIG. 1O. Sleeve 166 is then rotated in the direction shown by arrow 172 to raise it and hooks 164 enough to expose press-pad 142b so that an ear 146b can be located between press-pad 142b and sample collecting cartridge 112b (FIG. 1 P); whereupon, clamp 114b is forcibly closed to drive spikes 120b through sample carrier 130b and into the ear 146b (FIG. 1Q). After sufficient time for blood collection, clamp 114b is re-opened to release the ear and to allow removal of carrier 130b (FIG. 1R) and sleeve 166 is counter-rotated in direction of arrow 174 to lower it and its hooks 164 and to bring hooks 164 into line again with shoulders 170 (FIG. 1S). The clamp is then re-closed to re-engage hooks 164 with their respective shoulders 170 in platen 116b to allow re-formed integrated cartridge 112c to be removed as a unit (FIG. 1T). In this way, the possibility of contact between the fingers of the user and spikes 120b is minimized at all times.

FIGS. 1U and 1V are enlarged details of device 110b fitted to lower and upper jaws 126b and 144b of clamp 114b, sample collecting cartridge 112b being shown in exploded form to show detail of the modified spikes 120b employed in this variant of Example 1. In this case, spikes 120b are struck from thin sheet metal to form a single crown-like ring of spikes. The sheet metal base (not shown) can be insert-molded into platen 116b, adhered to the platen or otherwise secured in any convenient manner known to those skilled in the art.

Example 2

The second example of a device and method of the invention will be described with reference to FIGS. 2A to 2G. In this example, the device 210 (see particularly FIGS. 2A-2C) is a spring-loaded sample-collecting cartridge 212 adapted to be used with a pliers-like clamp 214 in a similar way to cartridge 112 of the first example. In this case, cartridge 212 has an upper hollow box-like body 213 that surrounds platen 216 with its spikes 220, the top face 215 of body 213 having holes 217 through which spikes 220 can be extended. Conveniently, as shown, platen 216 is a snap-fit within the open bottom of body 213 and is able to slide upwards within body 213 against spring means, which in this case, is a sponge rubber or plastic ring 228. In this example, sample carrier 230 is also a card 232 with a barcode 236 and a window area that is covered with sampling media 240 that is arranged to lie on body top 215 opposite spikes 220. Carrier 230 is stuck to one side of body 213 in a detachable manner, the detached carrier being shown in FIG. 2B.

Thus, in this example, the aforementioned guard means is formed by the body 213 and the aforementioned holding means is formed by the adhesive or other means by which carrier 230 is attached to and located with respect to body 213

As in the first example (FIGS. 1A-1E), a removable press-pad 242 can be fitted to and removed from the upper jaw 244 of clamp 214 in separate actions from the fitting and removal of cartridge 210 to jaw 226. It is not necessary to remove press-pad 242 and cartridge 210 as a unit as suggested in the variants of the first example described above because body 213 serves as the guard means, spikes 220 being withdrawn into body 213 of device 210 after use and before removal. There is the additional benefit that the spikes 220 are also contained within body 213 when the device 210 is supplied so that the danger of contact with them before use is also minimized, The operation of device 210 of the second example and the method of sample collection is similar to that of the first example, but will be briefly described with reference to FIGS. 2C-2F. Cartridge 212 and press-pad 242 are separately loaded onto lower and upper jaws 226 and 244 (respectively) in the manner indicated above. The open clamp 214 is then placed around the animal's ear 246 [FIG. 2D] and forcibly closed thereon [FIG. 2E] to drive platen 216 upwards in body 215, compressing spring means 228 and forcing spikes 220 through holes 217 in body top face 215, through sampling media 240 and into—or through—ear 246. Clamp 214 is held closed for a few seconds to allow blood from the puncture wounds to ooze out into contact with sampling media 240. After which, clamp 214 is released and opened to free ear 246, allowing sample carrier 230 to be removed and stored and upper pressure pad 242 to be replaced as before.

Figure 2D:
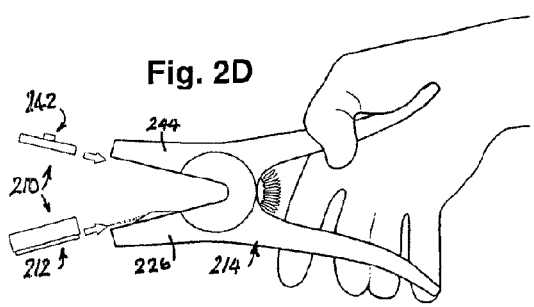
FIGS. 2A-2G depict the device of the second example of the invention.
Figure 2A:
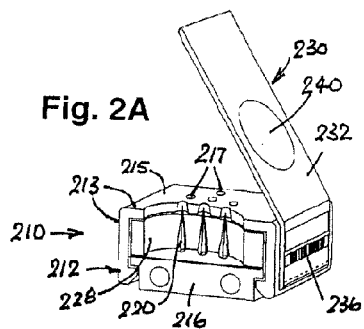
Figure 2E:
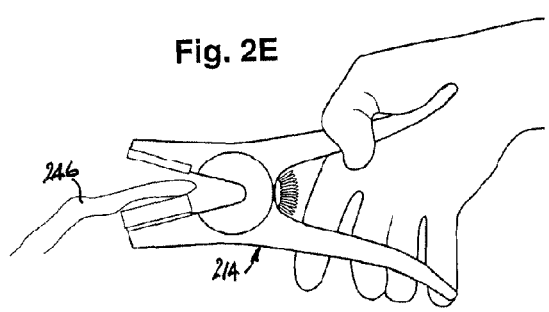
Figure 2B:
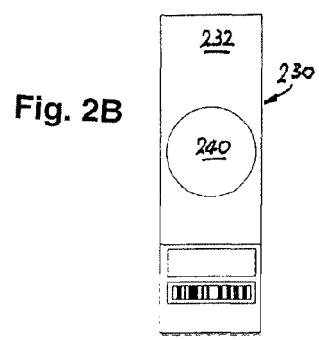
Figure 2F:
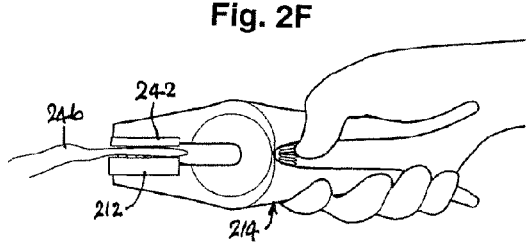
Figure 2C:
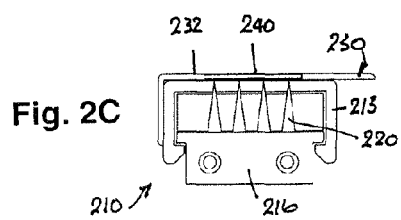
Figure 2G:
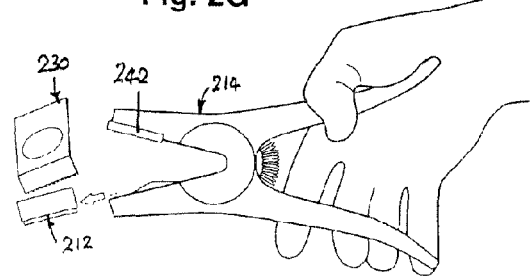

In this second example, however, rubber like spring means 228 acts as a vacuum pump as clamp 214 is opened that serves to draw blood from the ear wounds as platen 216 returns to the position shown in FIG. 2A. It is important to note that, in this position, the points of spikes 220 are beneath top face 215 of body 213 and, thus, guarded against contact with the user. [As noted above, body 213 and spring means 228 form the aforementioned guard means.]

Example 3

Figure 3A:
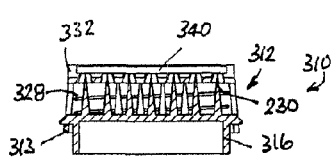
FIGS. 3A-3H depict the device of the third example of the invention.
Figure 3E:
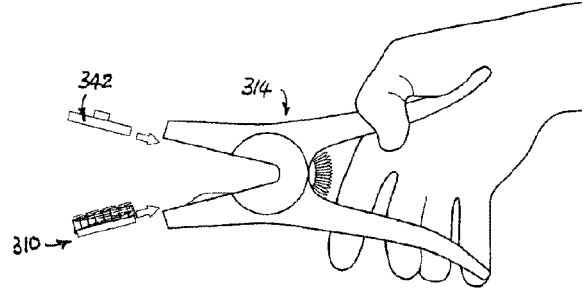
Figure 3B:
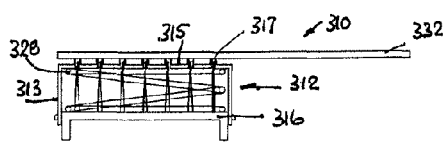
Figure 3C:
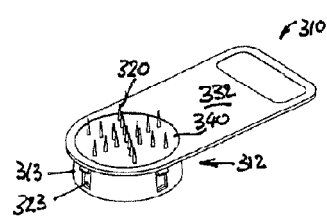
Figure 3F:
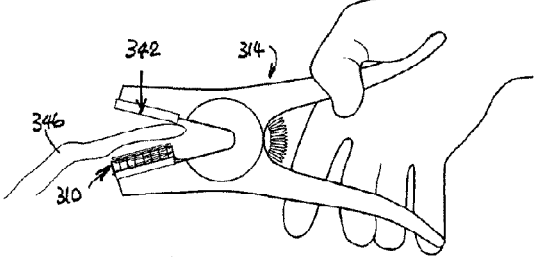
Figure 3D:
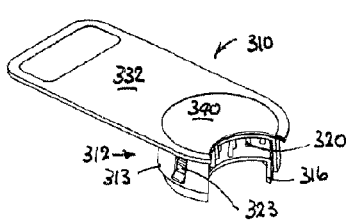
Figure 3G:
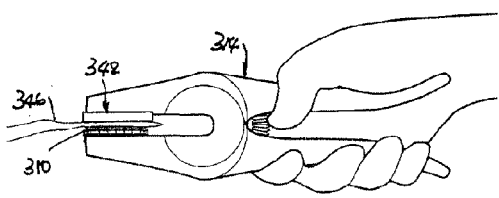
Figure 3H:
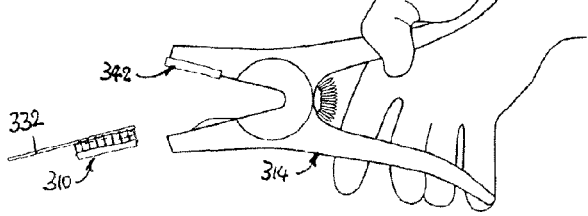

The device 310 of third example is illustrated in FIGS. 3A-3G and differs from the first two in the design of the cartridge 312. Since this cartridge is used in much the same manner as that of the second example, the clamp and method of use will not be described again. As in the second example, cartridge 312 has a body 313 with an upper face 315 having holes 317 aligned with spikes 320 that are mounted on a platen 316 which is spring-loaded downward away from upper face 315 by a helical steel spring 328. In this case, platen 316 is again snap-fitted within body 313 which has axial grooves 323 in its sides. A carrier card 332 is again adhered to top face 315 with a window of sampling media 340 located over spikes 320 so that the spikes will pass through sampling media 340 en-route into the ear and blood will be collected on sheet 340 from the resulting wounds. [FIG. 3C shows how spikes 320 would appear when pressed up through material 340, the ear 346 of the animal and clamp 314 not being shown in this view.]

As in the second example, opening of the clamp 314 after a sample is taken allows platen 316 and its spikes 320 to retract under the force of spring 328 to guard the tips of the spikes from contact with other bodies. Thus, cartridge 312 can be safely removed from lower jaw 326 of clamp 314. As in Example 1 (and 2), a replaceable upper press-pad 342 can also be removed or left in place depending on whether spikes 320 are designed to fully penetrate the animal ear 346 or not.

It will be appreciated that, in this example, the combination of body 313 with the platen and spring 328 serve as the aforementioned guard means and that carrier card 332 forms the aforementioned holding means by which the sampling media is held against the sample site and also located relative to the spike means (formed by spikes 320).

Example 4

Device 410 of the fourth example will be described in a little more detail with reference to FIGS. 4A-4F because it works a little differently from the preceding examples. The sample collecting cartridge 412 of this example is similar to cartridge 312 of the third example except that it has been inverted and the body 413 is molded integrally with an elongate upper arm 423 of a spring clip 425 so that platen 416 is driven downward by the upper jaw 444 of clamp 414 to move spikes 420 downward against a steel spring 428 through holes 417 in arm 423. Spring means 428 located within body 413 biases platen 416 upwards. A sample carrier 430 comprising a card 432 having a window of sheet like sampling media 440 is slidably mounted by brackets 441 (molded integrally with clip arm 423) immediately below holes 417 and body 413 of cartridge 412.

Spring clip 425 has an elongate lower arm 427 that is opposed to upper arm 423 and integrally joined to upper arm by a stiff back portion 447. A retrieval cord 428 is attached to back portion 447 of clip 425 for reasons that are explained below. As will also be best seen from FIG. 4G, upper jaw 444 of clamp 414 has a cylindrical projection 429 on its bottom face that is adapted to engage with and within cup-like platen 417 so as to locate clip/cartridge assembly 425/412 relative to clamp 414. Upper face of lower jaw 426 of clamp 414 carries a resilient press pad 442 opposite to projection 429.

In operation, clip/cartridge assembly 425/412 is placed within open jaws 444 and 426 of clamp 414 so that projection 429 is located within platen 416, the fit preferably being such that clip/cartridge assembly 424/412 is retained by friction against gravity in the position shown in FIG. 4G. Sample carrier 430 is then slid into brackets 441 on bottom of clip upper arm 423. Clamp 414 is then held on one hand while the ear if of the animal (not shown) is held by the other and brought into clip 425 between arms 423 and 427 so that portion of the ear is below sample collecting means 430. In bringing the ear into this position, arms 423 and 427 will have to be forcibly moved apart so that the ear is gripped firmly but not painfully by spring clip 425. Clamp 414 is then forcibly closed onto the ear, driving spikes 420 in cartridge 412 through holes 417 and sampling media 440 into the sample site on the ear.

Immediately thereafter, clamp 414 is released while the user also holds clip 425 closed onto the ear, thus permitting the spikes 420 to be withdrawn from the ear under the combined effect of spring 428 and the frictional engagement of projection 429 with platen 416. This combined action then effects the disengagement of projection 429 from platen 416 and allows the clamp to be removed clear of the ear while clip 525 is left in place for a few seconds to permit blood to flow into sampling media 440. Meanwhile, the operator lets go of the ear and clip 425 while retaining hold on retrieval cord 428 and, when sufficient time is judged to have elapsed for blood flow, cord 428 is pulled to remove clip 425 from the ear and allow (i) retrieval and hygienic packing of sample carrier 430 and (ii) safe disposal of clip/cartridge assembly 425/412. It will again be noted that automatic withdrawal of spikes 420 back into body 413 ensures that the operator cannot come into contact with the spikes.

It will be again seen that body 413 (in cooperation with platen 416 and spring 428) forms the aforementioned guard means, that the holding means is formed by the combination of carrier card 432 and locating brackets 441, and, that the aforementioned attachment means (whereby the sampling media can be held in contact with the site after withdrawal of the spikes) is formed by clip 425.) It is also worth noting that the entire clip and body assembly can be regarded as the device in this case.

Example 5

The device 510 of the fifth example, like that of the fourth example, is one where the sample collecting cartridge 512 is integrated with a spring clip 525 but, in this case, the arrangement is such that no clamp is required to press the spikes 520 into the ear of the animal (not shown). A further distinction is that spikes 520 are longer than those of Example 4, being intended to pass right through the ear and to form puncture wounds on both sides. Accordingly, the sample collector or carrier 530 is bifurcated having upper and lower card-like arms 532a and 532b joined by a common back portion 532c, each arm 532a, 532b having a window of sheet sampling media 540. Upper carrier arm 532a engages with longitudinal brackets 541a on underside of upper clip arm 523 while lower carrier arm 532b engages with similar brackets 541b on upper side of lower clip arm 527. This ensures that carrier arms 532a and 532b are held in place while spring clip 525 is forced over the animal's ear. Spring clip 525 has a rear portion 547 that has an aperture 547a from which carrier 530 can be withdrawn, the back portion 532c of carrier 530 extending through aperture 547c to allow it to be gripped for withdrawal.

Preferably, carrier 530 and combined clip-cartridge assembly 525-512 are supplied pre-assembled as a single unit. Furthermore, carrier 530 is supplied with upper and lower rolls 550a and 550b self-adhesive sheath strip material 551a and 551b for carrier 530, the lead portion of sheaths 551a and 551b being attached to respective sides of back portion 532c of carrier 530. FIG. 5A shows sheaths 551a and 551b applied to either side of carrier 530 as it is being withdrawn from clip 525 after use. FIG. 5G shows the carrier after removal and pressed together so that sampling media 540 is completely enclosed.

Again, cartridge 512 is integral with clip 525 with at a least portion of body 513 being molded integrally with upper clip arm 523 or snapped thereto, which is again perforated with holes 517 that take spikes 420 that are mounted on a movable platen 516. In this case, however, the inward or penetrating movement of platen 516 is effected by a driver spring 552 that is released from its normally compressed condition by manually operable triggers 554. When platen 516 reaches the full extent of its downward travel (ie, when the tips of spikes 520 have passed right through the ear), the pre-compressed withdrawal spring 528 is released automatically by contact of platen 516 with a return trigger 556. It should be noted that lower arm 527 of clip 525 has a hole (not visible in the drawings) opposite cartridge 512 so that spikes 220 do not strike lower arm 527 as they extend from the ear and pass through lower sampling media 540.

In use, device 510 of the fifth example is held in one hand and pushed onto the ear (not shown) while holding the ear in the other hand. The thumb or a finger of the hand holding the device is then used to operate driving spring trigger 554 to (i) drive platen 516 downward in body 513 and to cause spikes 520 to penetrate the ear and through both sheets of sampling media 540, and then (ii) automatically release return spring 528 to return platen 516 and withdraw spikes 520. Device 510 is left on the ear for sufficient time to allow blood to emerge from the wounds and to be adsorbed by sampling media 540 (on both upper and lower arms 532a and 532b) on carrier 530. The rear portion 547 is then held in one hand while the back portion 532c carrier 530 is grasped and withdrawn, the upper and lower arms 532a and 532b are then immediately pressed together to compete the sheathing action and to generate the sealed sample of FIG. 5G. After which, the remainder of the device can be retrieved from the ear and disposed of (again without danger of injury to the user from spikes 520). Alternatively, the entire device 510 may be removed as a unit by the use of a retrieval cord (not shown) in the manner described in the fourth example, and then, the sample carrier 530 can be removed and sheathed while off the animal.

Figure 5I:
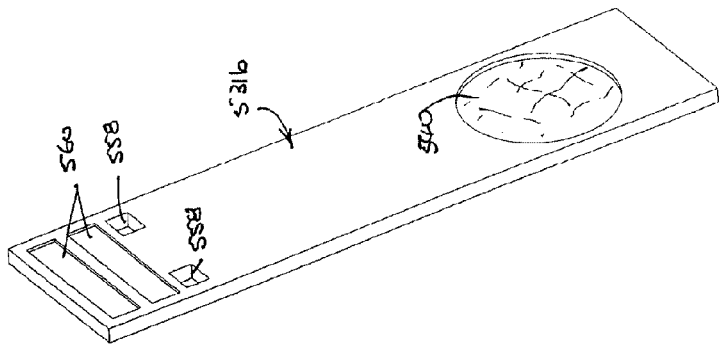
Figure 5F:
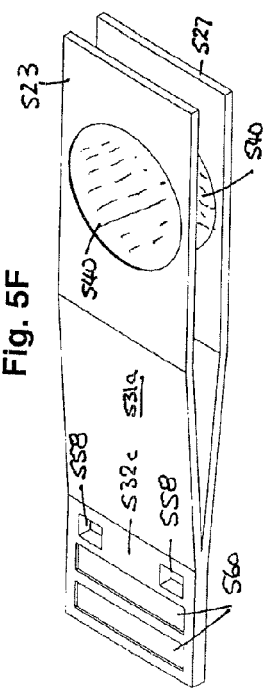
Figure 5G:
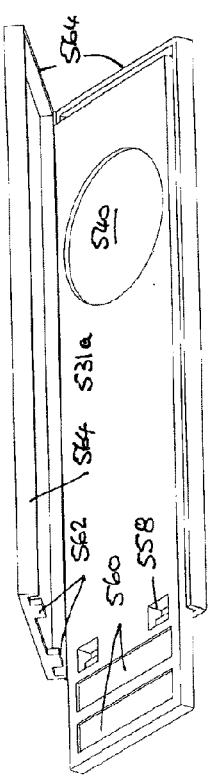
Figure 5H:
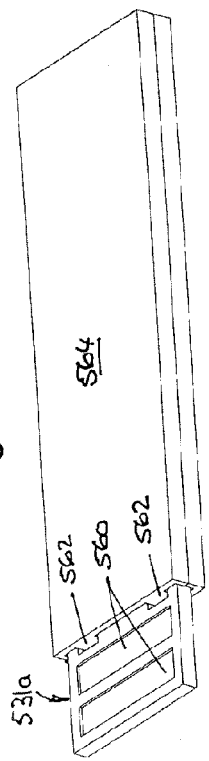

Alternative carriers and protection means are illustrated in FIGS. 5F-5I. A first alternative (unsheathed) bifurcated carrier 531a is shown in FIG. 5F from which it will be seen that it differs from carrier 530 only in that the common back portion 532c is perforated with holes 558 and has rectangular recesses 560. Holes 558 are arranged to interlock with protrusions 562 in a hinged box-like cover 564 (FIG. 5G) that can be snapped closed over carrier 531 (when compressed or flattened), as shown in FIG. 5H. Recesses 560 are designed to accommodate identification information such as a barcode, RFID device and/or handwriting. A second alternative carrier 531b is shown in FIG. 5I, differing from carrier 531b only in that it is not bifurcated. This type of carrier can be fitted under the bottom face of the upper arm 523 of clip 525 and/or on the top face of lower clip arm 527. It can also be accommodated in cover box 564 in the manner described above.

Again, the guard means of Example 5 is formed by the operation of body 513, withdrawal spring 528 and face 517, while the holding means is formed by carrier 530 and guide brackets 541a and 541b, and clip 525 serves as both the attachment means and the clamp means. The combination of the clip and body can also serve as the device in this case.

Example 6

As will be seen from the staged drawings of FIGS. 6A-6F, the device 610 of the sixth example is similar in operation to that of the fifth example in that it is an integrated cartridge (612) and clip or clamp (625) that is pushed onto the ear 646 of the animal, spring-loaded spikes are driven into the ear and then quickly and automatically retracted, the device remains in place on the ear while blood is collected on sampling media, the device is removed and the sample recovered. If a thin portion of the ear is selected, the spikes may be driven right through the ear or, if a thick portion is selected, the spikes need only partially penetrate the ear. However, the manner in which the device is attached to the ear and the manner in which the sample is retrieved differ from the preceding example.

Referring more specifically to the drawings, the device comprises a hinged tong-like clip 625 having an upper arm 623 and a lower arm 627. Cartridge 612 is a separate spring-loaded unit like that [512] of the fifth example that is preferably supplied attached to upper arm 623 by means of a slider 666. As best seen from the sectional drawings of FIGS. 6G, the bottom of cartridge body 613 has an annular flange 667 so that the cartridge can be entered upwards through a hole 668 in upper arm 623 which has a locating recess 669 for flange 667, the cartridge being retained in this position by slider 666. The sampling media 640 for collecting the blood is in the form of a disk that is fitted into flange 667 so that will be penetrated by the spikes (not shown). A hole 670 is also formed in lower arm 627 opposite hole 668 in upper arm 623 to accommodate spikes protruding through the ear, it being convenient to make hole 670 large enough to allow cartridge flange 667 to pass so that cartridge 612 can be loaded and unloaded into upper arm 623 without having to open clip 625. Finally, a sliding lock-ring 672 is fitted over clip 625 so that the arms of the clip can be forcibly closed (and held closed) by sliding the clip forwards (toward the open end of the clip).

Thus, in use, assembled device 610 is slipped over the ear 646 with lock ring 672 in the rear position (FIG. 6A) and lock-ring 672 is forced forwards along clip 625 so as to clamp ear 646 (FIG. 6B), whereupon, trigger 654 is activated to cause the spikes of cartridge 612 to be rapidly extended into and then withdrawn from ear 646. After sufficient time to permit blood flow, lock-ring 672 is withdrawn to release the pressure on the ear (FIG. 6C) and the ear is released (FIG. 6D). Slider 666 is then moved to the rear and cartridge 612 released (FIG. 6E and 6H). The clip 625 can then be re-closed for storage and re-use with a new cartridge if desired (FIG. 6F).

Since clip 625 again serves as the attachment means by which the adsorbent material can be held onto the site after withdrawal of the spikes, it may be desirable to avoid the need for the clip to be held in place on the ear by hand while blood exuding from the site is collected by the sampling media. In that case, a retrieving strap or string (like strap 428 of Example 4) may be employed but, in this case, it will be desirable to attach it to clamp ring 672 so that pulling on the strap will move the ring to its release position and allow the clip to open, thereby avoiding the need to drag the sampling media across the surface of the ear.

Example 7

Figure 7A:
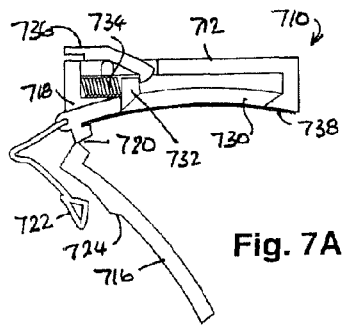
FIGS. 7A-7H depict the device of the seventh example of the invention.
Figure 7F:
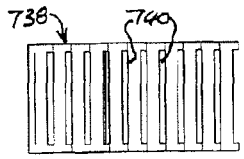
Figure 7B:
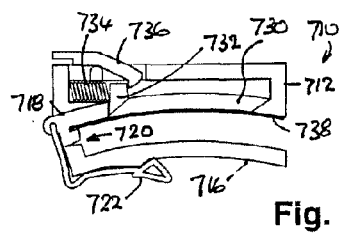
Figure 7G:
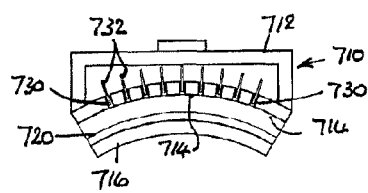

The device 710 of this example differs considerably from those of the previous examples in that it is a compact assembly which clamps on the ear and in that the ear is cut rather than spiked. This device will be described with reference to FIGS. 7A-7H and a variant will be described with reference to FIGS. 7I to 7M. FIGS. 7A-7E are longitudinal sections of the device, while FIG. 7G is a transverse section (the sections not being hatched).

Figure 7C:
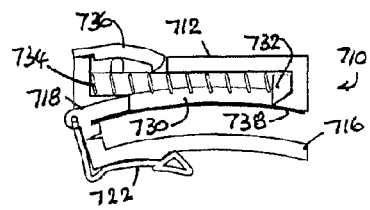
Figure 7D:
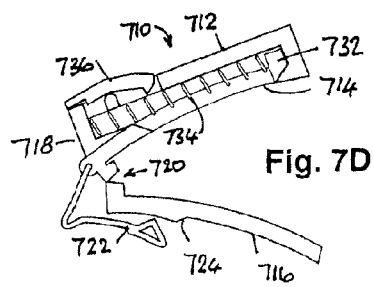
Figure 7H:
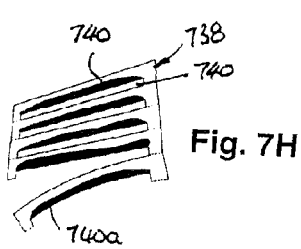
Figure 7E:
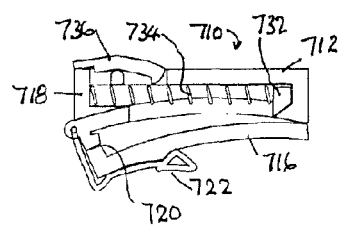

Device 710 has a hollow molded plastic body 712 with a concave bottom face 714 and a clamp arm 716 is attached to one end 718 of body 712 by an integral hinge 720. A wire clip 722 is hinged to end 718 and shaped so that, when forced over a shoulder 724 on the outside of arm 716, an animal ear (not shown) can be firmly clamped between arm 716 and bottom face 714 of body 712. FIG. 7A and 7D show arm 716 and clip 722 in the 'open' or non-clamping position, FIGS. 7B and 7C show arm 716 in the clamping position where the ear (not shown) is in place and FIG. 7E shows the position of the arm in the closed or clamping position without the ear in place.

Bottom face 714 of body 712 is has a number of parallel longitudinal slots 730 with a corresponding number of short blades 732 slidably mounted therein, blades 732 being joined together (in a manner not shown) so that they will slide as a unit, and, being biased to travel away from body end 718 by a compression spring 734. As supplied, blades 732 are held against such movement by a manually operable catch lever 736. Affixed to bottom face 714 of body 712 is a sheet of adsorbent material 738, which is preferably has narrow preformed slots 740 therein (see FIG. 7F) that accommodate respective ones of blades 732 when sheet material 738 is in position. Pre-slotting ensures that blades will not catch or tear the material as they move. As indicated, material 738 is pre-attached to bottom face 714 of device 710 as it is supplied for use Device 710 may be used in the following manner. With clamp arm 716 in the open position as in FIG. 7A, body 712 is placed on the animal's ear with an edge of the ear close to hinge 720 and with arm 716 hanging down and below the ear. The arm is then closed on the ear to hold it firmly and clip 722 snapped into place as in FIG. 7B. Catch lever 736 is then operated to release blades 732 which cut through the upper portion of the ear near the center of the curved bottom face 714 by virtue of the curvature and then move to a shielded position to the end of body 712 opposite end 718. Device 710 is left in place until blood exuding from the resulting wounds is collected by sampling media 738. After which, clip 722 is released and arm 716 opened to allow removal of the device from the ear. It should be noted that curving the ear so that the convex side is the cut side tends to open the wounds and to encourage blood flow from the wounds. Material 738 may then be removed, the resultant blood samples being shown at 740 in FIG. 7H. If desired, an individual sample 740a can be readily separated from the remainder of the material 738.

The variant of device 710 will now be described with reference to FIGS. 7I to 7N, with corresponding parts given the same reference numbers but with the suffix 'a' added. As will be seen from FIGS. 7I-7M device 710a is very similar to device 710 in longitudinal cross-section, the principal differences being the use of a draw-string 750 to drive a single blade 732a from right to left and the use of filtered vents 752 and 754 on the top of molded plastic body 712a and on the bottom of clamp arm 716a. Since only a single blade is employed, body 712a can be much narrower and the entire device can be much lighter than that of Example 7. This makes it less annoying to the animal when attached to an ear so that it is more easily retained on the ear during the time needed to allow blood collection. A further difference in this example is that sampling media 738a is supported by a carrier 756 which is slidingly fitted into grooves in body 712.

Blade 732a is mounted on a slider 752 that is guided for movement along slots or grooves 760 within body 712a. When blade 732a had been pulled fully to end 718a of body 712a (to effect the cut in the ear at the sample site), it is locked in that position by a barb-like catch 762.

The operation of device 710a is essentially the same as that of device 710, but is indicated as follows: With clamp arm 716a in the open position [FIG. 7I], body 712a is placed on the animal's ear with an edge of the ear close to hinge 720a and with arm 716a hanging down and below the ear. The arm is then closed on the ear to hold it firmly and clip 722a snapped into place [FIG. 7J]. Draw-string 750 is then operated to pull blade 732a to end 718a of body 712a where it is retained by catch 762 [FIG. 7K]. Device 710a is left in place until blood exuding from the resulting cut is collected by sampling media 738a. After which, clip 722a is released and arm 716a opened to allow removal of the device from the ear [FIG. 7L].

In the case of this variant, however, arm 716a is re-closed to encase carrier 756 and sampling media 738a for transport to the laboratory. With this in mind, a number of desirable modifications can be made to device 710a. First, integral hinge 720a can be replaced by a spring hinge that allows the left end of arm 716a to separate from the rest of body 712a in order to accommodate the ear but to spring back to securely enclose carrier 756 and material 738a. For that purpose, a separate clip can be used on the right hand end of arm 716a to secure that end to body 712a after the sample has been collected. The seal around the periphery of carrier 756 can be enhanced by forming the frame of carrier 756 from resiliently deformable material and by the use of a thin rubber-like boot 760 (shown only in FIG. 7N in broken lines]. It is then desirable to ensure that the fresh sample is vented to atmosphere so that it can dry out, which reduces bacterial and mould growth within the sample and meet regulatory restrictions regarding the transport of wet blood. Filtered vents 752 and 754 in body 712a and arm 716a serve that purpose while inhibiting bacterial and mould contamination from the atmosphere.

Example 8

The device 810 of this example is similar to those of examples 1 to 6 in having a cartridge and press pad that are clamped together but includes a means to retain the device on the ear of the animal after removal of the clamping device whilst blood is being collected by the sampling media. This device will be described with reference to FIGS. 8 through to 16.

Referring to FIGS. 8 to 16, the device 810 includes a cartridge 812 and a press pad 814, joined together by strap 816. Preferably the shell, strap and press pad are formed integrally and more preferably formed by plastics injection molding.

A separate sample carrier 818 is snap fitted to the base of the cartridge 812 with tabs 820 of the sample carrier engaging with annular rim 822 of cartridge 812. If desired the rim 822 may be discontinuous, allowing the carrier 818 to be removed by rotation relative to the cartridge 812. Other methods of attachment of the carrier 818 to the cartridge 812 may be used.

In this example, the carrier 818 includes a card 824 providing space 826 on which the user can write and a circular window area 828 that is covered with sheet like sampling media 830. The sampling media 830 has a central aperture 832. The carrier may include a bar code, written identification and other data as desired.

The cartridge 810 includes cylindrical shell 834 and a platen 836 located within the shell. The platen 836 is moveable along the length of the shell 834 and is biased upwards by helical spring 838 located between the lower surface 840 of the platen and the base 842 of the cartridge 812. The upper end of the shell has an inward extending rim or shell 827 that limits upwards movement of the platen and defines a central aperture 864. Preferably the central aperture limits access to the platen so that a user cannot easily depress the platen except with the intended tool. The platen has tabs 829 that slide in slots 831 in the shell. These tabs 831 prevent the platen rotating within the shell and control vertical movement of the platen. Other means for controlling rotation and vertical movement may be used. For example, the wall of the shell may have one or more vertically extending ribs that locate the platen. The base 842 is a separate component and is preferably a snap fit into the lower end of the shell. Alternatively, the base may be formed integral with the side walls of the shell and a cap attached or mounted on the upper end of the wall. Spike means, comprising two diametrically opposed blades 844a and 844b, extend from lower surface 840 of the platen 836. In plan view, as seen in FIG. 9b the blades 844 are arc shaped. In side view, as seen in FIG. 9a, the lower edges 846a and 846b are also curved. This is to aid cutting of the animal's ear, as described later. Other configurations and more than two blades may be used, as will be described later.

The blades 844 may be formed integrally with the platen. Further, whilst the embodiment uses blades, other spike means, such as the spikes of examples 1 to 6 maybe used instead. As with the other examples, the spike means may comprise an array of spikes or blades formed by plastic injection molding, by the insert molding of metal elements into a plastic platen, by metal die-casting or by stamping, folding, or upsetting of sheet metal by techniques known in the art.

The base 842 of the cartridge has two arcuate slots 848a, 848b and a central circular aperture 850. The blades 844a, 844b extend through the two arcuate slots 848a, 848b, respectively, when the platen 836 is depressed. When the platen is fully raised, as seen in FIG. 11c, the blades 844a and 844b are fully retracted within the cartridge 836. The shell and base can thus be considered to be the guard means of the invention.

The platen has a central extension 852 that extends downwards through the center of the helical spring 838. The upper end of the extension is hollow and has a central bore 854. This bore 854 is shaped to receive an adaptor 856. The lower part of the extension is solid and defines a pin 858. The pin 858 has a shank 860 and an arrow shaped head 862 at the lower end of the shank 860. The pin 858 is preferably formed integrally with the platen but may be a separate component.

As seen in FIG. 11c, when the platen is fully retracted part of the shank 860 and all of the head 862 extends through the aperture 850 in the base and through the aperture 832 of the sampling media. This is not essential and, if desired, the shell may be made taller so that all or substantially all of the pin is within the cartridge. The central aperture 864 is sized to allow the adaptor 856 to pass there-through and press upon the platen 836.

As seen in FIGS. 10b and 9c the adaptor 856 has an annular flange 866 that overlies the part of the annular disc of platen around the bore 854 and a central pin 868 that extends into the bore 854. Preferably the free end of the pin 868 engages the blind end of the bore. Force applied to the adaptor is thus transferred to the pin and the blades via the annular disc of the platen.

The external shape of the adaptor 856 preferably closely matches the internal shape of the bore and is a snug fit within the bore. Thus, when the adaptor is inserted into the bore, the cartridge is retained on the adaptor by friction against the effects of gravity and normal movement. Other methods to temporarily retain the cartridge on the adaptor may be used.

The press pad 814 is generally rectangular and has a keyhole shaped slot 870 intended to receive the pin head 862. The slot has oval end portion 872, a necked portion 874 and a divergent portion 876. The size of the head 862 is larger than the width of the oval end portion 870 whilst the shank 860 is smaller. The material of the press pad is resilient. Accordingly, the head 862 may be pushed through the end portion 872 under action of the adaptor, with the material returning to its original position and resisting withdrawal of the head vertically through the slot. The necked portion 874 has an opening that is smaller than the diameter of the shank 860 and so resists movement of the pin along the slot. Thus, once the head has passed through the end portion 864, the pin head is retained until sufficient force is applied (by the user) to move the pin either along the slot or vertically back out of the slot. As will be explained further, in use this will usually only occur as a deliberate action by the user.

The press pad 814 has two parallel and longitudinally extending openings 876 by which it may be mounted on prongs 878 mounted on the lower jaw 880 of a conventional ear tagging gun 882. Other means to mount the press pad on a tagging gun may be used.

In use the adaptor 856 is mounted on the free end of the plunger 884 of ear tagging gun 882. Alternatively the plunger may be modified to have an end similar to that of the adaptor. The adaptor 856 is intended to remain on the plunger 884 for multiple uses and is preferably affixed thereto semi permanently. Most ear tagging guns have an internally threaded bore into which a threaded end of the adaptor is screwed. The adaptor may be attached to the plunger by other means or combination of means. For example, the adaptor may have a blind bore into which the free end of the plunger is received.

For use, the device 810 is mounted on the tagging gun, with the cartridge 812 mounted on the adaptor 856 and the press pad 814 mounted on the prongs 878 of the opposed jaw 886 of the tagging gun, as seen in FIG. 15a. In this position the pin 858 is opposed and aligned with the end section 872 of the slot 870 on the press pad 814. The platen and the blades are fully retracted and so there is no risk of cutting to the user as the cartridge 812 is placed on the adaptor 856.

The tagging gun 882 is positioned around an animal's ear 888 (FIG. 15b) and the user compresses the handles 890 to clamp the animal's ear between the cartridge 812 and press pad 814. This causes the plunger 884, with the adaptor 856 and cartridge 812, to move towards the opposed jaw 880, initially clamping the ear 888 between the press pad 814 and the pin 858. Continued movement of the plunger towards the jaw 886 causes the pin 858 to pass through the animal's ear and into the end portion 872 of the slot 870 in the press pad, with the carrier 818 pressed against the animal's ear, as shown in FIGS. 9a to 9c and 15c.

Simultaneously, the blades 844 extend out of the openings and pass through the sampling media 830 and cut into the surface of the animal's ear, causing bleeding. If desired, the sampling media may be pre-cut or otherwise weakened to allow passage of the blades and prevent or minimize tearing.

The plunger depresses the platen, and with it the blades and pin, downwards until movement of the platen is limited by the blades contacting the press pad or the tabs 829 contacting the bottom of the slot 831. Which of these actions occurs first depends on the thickness of the animal's ear. If it is likely that the blades will contact the press pad, preferably the blades and press pad are configured and/or made of material that will resist deformation of the blades. If it is desired that the blades pass all the way through the ear, the press pad may be provided with slots or recesses to allow the ends of the blades to pass below the general surface of the press pad. If the slots 831 are omitted a stop, such as an inwardly extending annular flange, may be formed on the inner surface of the shell 834 to limit downwards movement of the platen 836, if this is desired.

Continued squeezing of the handles together results in the retraction of the plunger 884 and the adaptor 856. This results in disengagement of the adaptor 856 from the platen 836, as seen in FIGS. 10a-c and 15d. The cartridge 812 remains attached to the ear because the pin 856 is trapped by the press pad 814.

Retraction of the plunger allows the platen to move away from the ear, under the action of the spring 838, until the annular flange of the head 858 bears against the underside of the walls surrounding the slot 870. The annular flange on the rear face of the head prevents the spring 838 from withdrawing the head 862 through the opening. At this point, for most animals, the blades have retracted back into the cartridge, allowing the cuts in the ear to bleed directly onto the sampling media 830. It will be appreciated that a very thick ear may result in the blade still be extended into the flesh at this point, but this is not critical. Further, the length of the pin and hence the space between the press pad and lower surfaces may be varied for different species and/or breeds if this is an issue.

Because the pin 858 is trapped by the press pad 814, the cartridge and the sampling media remain secured and squeezed firmly against the animal's ear. The pin 856 extends through the animal's ear and so the cartridge cannot move relative to the ear. The spring 838 acting between the platen 836 and the base 842 of the cartridge acts to squeeze the animal's ear 888 between the base 842 and sampling media 830 on one side and the press pad 814 on the other side.

The device 810 is then removed from the tagging gun by slipping the press pad from the jaw adaptor and left secured to the animal's ear, as shown in FIG. 15e. The device 810 is left for a time, usually about 25 to 30 seconds, which is usually sufficient for an appropriate amount of blood it to be collected by the sampling media. The device 810 is then removed by the user.

Referring to FIGS. 10a to 10f and 15f, to remove the device 810 from the ear the user preferably slips a finger 890 into the loop formed by the strap and pulls backwards, as indicated by arrow 892. This causes the press pad 814 to slide backwards relative to the cartridge 812 and the pin 858. If necessary the user may hold the cartridge shell 834 to aid this relative movement.

The pulling action causes the pin 858 to move relative to the press pad 814 along the slot 870 past the necked region 874. Once the pin 858 has passed the necked region to a point where the slot is wider than the size of the head the press pad is free to fall away from the pin and/or the pin 858 is automatically withdrawn vertically from the slot 870, under the upwards force of the spring 838, depending on the strength of the spring. Alternatively the pin may be removed from the end of the slot. Once the head is free of the slot, if the spring is strong enough, the spring may cause the platen and pin to move upwards, withdrawing the pin back through the ear of the animal and the sampling media. In the present embodiment the spring is not strong enough, the pin remains in the ear and the user merely grasps the cartridge 812 and pulls it from the animal's ear. This frees the device from the animal's ear, as shown in FIGS. 11a to 11c and 15g.

The carrier 818 may then be removed from the cartridge (FIG. 15h) and placed in a suitable container for transport to a laboratory or other location for further processing. The cartridge 812 and press plate 814 assembly may then be disposed in a suitable container. If desired the press pad may be pressed against the cartridge so as secure the pin head in the end of the slot, so shielding the user from the pin.

Whilst the head will be bloody, because the pin is a relatively coarse piecing implement that requires a relatively large force to be driven through the animal's ear, the risk of scratching the user by the exposed pin head is relatively low.

If desired the entire device 810 may be stored and transported for subsequent separation and processing.

Whilst an offset strap 826 is shown, if desired, two straps, which extend on either side of the tagging gun may be provided. By providing two straps, when the user pulls on the straps to release the device from the ear, the pulling action will be generally aligned with the direction of the slot 870. Alternatively, if a single strap is used, the direction of the slot 870 may be angled to the general direction of the two openings 876 and more aligned with the general direction of pull out of the single strap. If desired the strap may extend from the center region between the two openings 876 of the press pad rather than from the side.

Whilst the embodiment of the eighth example is intended to be applied with a conventional ear tagging gun it may be modified for stand alone use. Further, the action of driving the retaining pin through the animal's ear into a press pad may be separated from the action of driving the blades into the flesh of the ear.

Thus, for example, the pin may be formed separate from the platen and provided with separate drive means, such as a preloaded spring, to drive it through the ear of the animal and into a press pad that retains the pin. A spring clip, similar to item 412 of the fourth embodiment, may be used to position and/or retain the press pad in the correct alignment with the upper cartridge, with the press pad mounted on the underside of the clip. The platen and blades may then be separately driven into and withdrawn from the ear. The mechanism of the fifth example is one that may be used for this purpose.

The device of the eighth example is preferably configured to be a single use device, to prevent the cartridge being used on multiple animals, albeit with a new carrier and sampling media. If desired the internal surface of the shell may be provided with locking means to lock or otherwise retain the platen in a retracted position after use. One such locking means comprises an annular flange near the upper end with an angled lower surface, which allows the spring to drive the platen past the flange during the act of withdrawal.

Other means of retaining and releasing the cartridge from the press pad may be utilized. For example, the pin 862 may be provided with a non circular head that is received and retained in a corresponding recess in the press pad. By providing the shank of the pin with a line or point of weakness the pin head may be broken off the shank by rotation of the press pad relative to the cartridge, releasing the cartridge. This also prevents the device being reused. The pin head may be removed in other ways, for example providing a blade for cutting the head from the shank.

The preferred spike means of the eight example form elongate cuts in the animal's ear rather than "pin" holes. Elongate cuts increase the probability of cutting a vein and so producing good blood flow. The arcuate shape of the blades is merely one configuration of many.

FIGS. 17a to 17f show various blade configurations. In FIG. 17a there are four straight blades 902a to 902d. All four blades are parallel to each other with the two inner blades 902b, 902c, coaxial and offset relative to the outer blades 902a, 902d.

In FIG. 17b there are two parallel and offset straight blades 904a, 904b.

In FIG. 17c there are two opposed blades, 906a, 906b. Each blade is formed of two segments 908a, 908b extending at an angle, preferably about 90 degrees, to each other.

In FIG. 17d there is a single U-shaped blade 910.

FIG. 17e shows a star shaped arrangement of five blades 912a to 912e. The number of blades may be from three upwards.

FIG. 17f shows an arrangement of two arcuate shaped blades 914a, 914b. In this variation the center of curvature of each of the blades is not the center of the platen, as in the main embodiment FIGS. 18a to 18d show various blade shapes. These shapes may, generally be used with any of the blade configurations previously described.

The blade 920 of FIG. 18a has a saw-tooth profile 922. The blade 924 of FIG. 18b has a convex profile 926. The blade 928 of FIG. 18c has a concave profile 930.

The double blade assembly 932 of FIG. 18d has two parallel blades 934a, 934b. The cutting edges 936a, 936b of the blades are not parallel to the base 938 but are angled in opposite directions relative to the base. The blade assembly shown is an integral unit that may be formed from a single piece of bent sheet metal. Alternatively, two separate blades may be provided that are mounted on or in the platen, without the base 938.

FIGS. 19a and 19b show a shutter arrangement in which a shutter 940 overlies the base 942 of the cartridge. The shutter has apertures 944 that correspond to the locations of the blades 946. The shutter is movable sideways relative to the blades between a first position, shown in FIG. 19a, in which it is offset relative to the base and the apertures do not align with the blades. In the second, operative position, shown in FIG. 19a, the apertures align with the blades, so allowing the blades to descend. In one of the positions the edge of the shutter is aligned with the edge of the cartridge. Thus it is relatively easy for the user to know which position the shutter is in. Whilst linear movement is preferred, other arrangements may be used. For example, a shutter that rotates about the center of the cartridge between operative and non operative positions may be provided.

Example 9

Figure 20A:
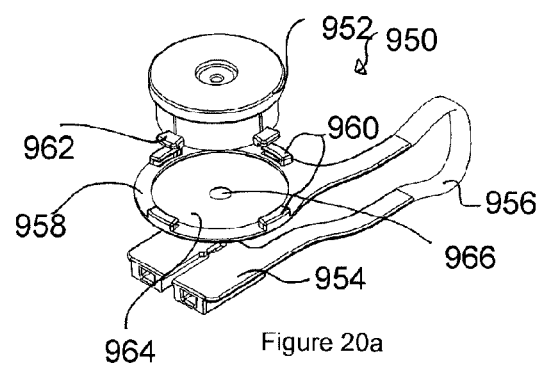
FIGS. 20a, 20b and 20c are, respectively, a partially exploded perspective view from above, a partially exploded side view and a partially exploded perspective view from below of a the ninth example.
Figure 20C:
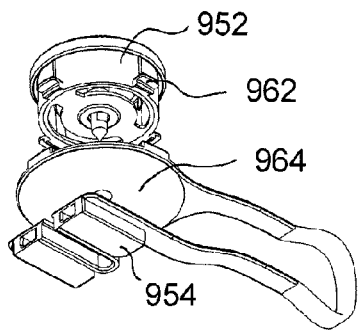
Figure 20B:
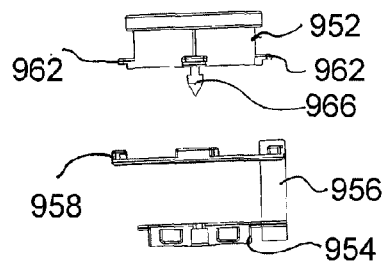

The device 950 of the ninth example, depicted in FIGS. 20a, 20b and 20c, is similar to that of the eighth example. The device includes a cartridge 952 and a press pad 954 joined together by a strap 956. The cartridge 952 is not, however, formed integrally with the strap 956. Instead the strap 956 includes an annular retaining ring 958 having retaining tabs 960. The cartridge 952 has tabs 962 that engage the tabs 960 on the retaining ring 958. These may be a snap fit. Alternatively the tabs 960, 962 may engage each other by rotation of the cartridge 952 relative to the ring 958.

The retaining ring 958 has sampling media 964 mounted on its underside. The sampling media 964 preferably has a central aperture 966.

The press pad 954 is substantially the same as that of the eighth example. Similarly the operation and internal arrangement of the cartridge 952 is substantially the same as that of the eighth example. Accordingly the cartridge 952 includes a platen (not shown) upon which are mounted blades (not shown) and a central pin 966 for engagement with the press pad 954.

The operation and use of this example is substantially the same as that of the eighth example, except that once the device has been removed from the animal the cartridge 952 may be removed from the remainder of the device and disposed of. The strap, press pad and sampling media may then be packaged and dispatched to a laboratory or the like.

Example 10

The device 1010 of the tenth example is depicted in FIGS. 21a through to 23.

The device 1010 has a cartridge 1012 with integral handle 1014 and integral cover 1016, the later joined to the cartridge by flexible hinge 1018. The cartridge operates similar to that of the eighth example in having a spring loaded platen 1020 having cutting blades 1024 and central pin 1026. The platen, blades and pin are depressed using an ear tagging gun, as described later.

The cartridge 1012 has sampling media (not shown) mounted on its bottom edge 1028. The sampling media is similar to that of the eight and ninth examples in being a circular disc with a central aperture to allow the pin 1026 to extend therethrough.

The cap 1016 swings between an open position, as shown in FIGS. 21 and 22, and a closed position, as shown in FIG. 23. In the closed position the cap engages the lower end of the cartridge and covers the sampling media and the pin 1026. A depression 1030 may be provided to accommodate the pin 1026.

Figure 24A:
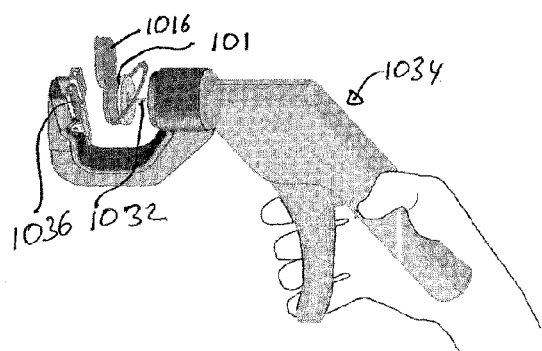
FIGS. 24a to 24e depict the steps of use of the device of the tenth example
Figure 24D:
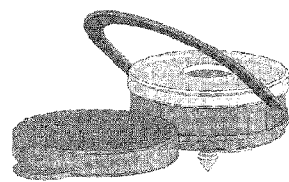

Use of the device 1010 is substantially the same as for the eighth example, and is depicted in FIGS. 24a through to 24

Figure 24B:
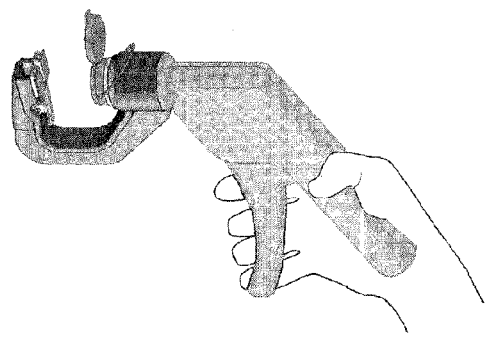
Figure 24E:
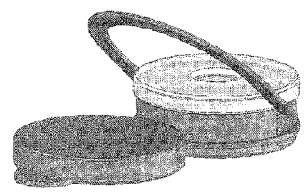
Figure 24C:
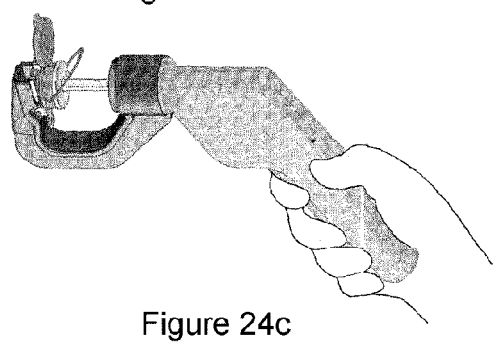

The device is provided closed, as in FIG. 23. After opening the cap 1016 the cartridge is mounted on the plunger 1032 of an ear tagging gun 1034 (FIG. 24a). The gun is then placed over the animal's ear (FIG. 24b) and the user compresses the handles to clamp the animal's ear between the cartridge and the lower jaw 1036 of the gun 1034 (FIG. 24c). If desired a separate press pad may be mounted on the lower jaw. As with the eighth example, this causes the pin 1026 to pass through the animal's ear and the blades 1024 to cut into the animal's ear. This fully extended position is shown in FIGS. 22c, 22d and FIG. 24c. Continued squeezing causes the plunger 1032 to retract.

At this point the pin has passed through the animal's ear and the head 1038 is on the other side of the ear. The spring in the cartridge urges the platen, blades and pin 1026 upwards, as described with reference to the eighth example. Whilst there is no press pad, the head 1038 is not withdrawn through the hole in the ear but engages the underside of the ear. The spring urges the sampling media against the upper side of the ear and blood is collected by the sampling media. After about 25 to 30 seconds the user merely grasps the cartridge 1012 or the handle 1014 and pulls the device from the ear. This causes the pin 1026 to be withdrawn through the hole in the ear. Once the pin head 1038 has cleared the ear, the spring in the cartridge fully retracts the platen, blades and pin back to the position shown in FIG. 21b. The user then closes the lid 1016 to enclose the sampling media. The lid may be a press fit, as shown, or may be provided with a catch to more securely close the lid. The device is then dispatched to a laboratory for further processing. At the laboratory the sampling media may be retrieved by opening the lid and withdrawing the sampling media.

Example 11

Figure 25A:
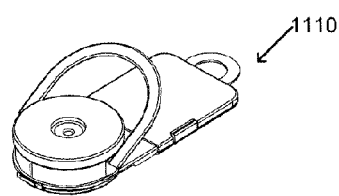
FIGS. 25a, 25b and 25c are, respectively, a perspective view from above, a side view and a plan view from above of the eleventh example in an initial state.
Figure 26:
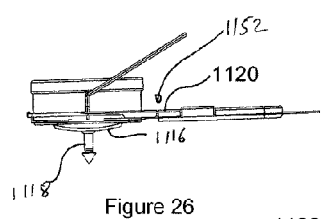
FIG. 26 is a side view of the eleventh example in an extended state.
Figure 27A:
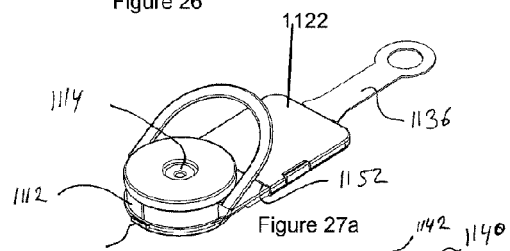
FIGS. 27a and 27b are, respectively, perspective views from above and below of the eleventh example in the retracted state.

The device 1110 of the eleventh example is shown in FIGS. 25 to 27. The device 1110 has a cartridge 1112 with a spring loaded platen 1114, blades 1116 and pin 1118 and is similar to the eighth to tenth examples in this regard.

A housing 1120 extends to one side from the lower end of the cartridge. The housing has a generally planar upper wall 1122 and a lower cover 1124. Side walls 1126 extend between the upper wall 1122 and cover 1124 and so define a space therebetween. The upper wall is attached to the cartridge whilst the cover 1124 is hinged to one of the side walls at 1127. The housing may be formed integrally with the cartridge or may be a separate component. The cover 1124 does not extend under the cartridge.

Located in the space upper wall 1122 and a lower cover 1124 is a carrier 1130 that carries a disc of sampling media 1134. The carrier 1130 may move longitudinally within the housing and has a handle 1136 that extends out of an opening 1138 in the end of the housing to allow the user to pull the carrier sideways. The handle 1136 has an end portion 1140 to enable the user to grasp the carrier, an elongated tab 1142 and a locking portion 1144. The tab is 1142 is slightly narrower than the opening 1138. The end portion is wider than the opening 1138, as is the locking portion 1144.

Figure 25B:
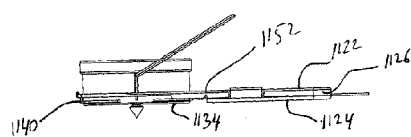
Figure 25C:
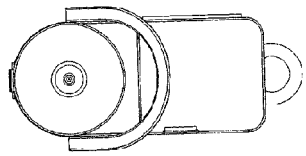

As assembled and ready or use the carrier is fully retracted in the housing with the cover closed, as shown in FIGS. 25a to 25c. In this position the sampling media 1134 lies under the cartridge. The carrier 1130 has a tab 1146 that extends upwards and overlies the wall of the cartridge. This tab 1146 prevents the carrier 1130 sliding out of the housing due to normal handling. In this position the end portion 1140 engages or is close to the end wall and so prevents the carrier sliding further inwards.

The device is similar to the tenth example in not having a lower press pad and relies on the pin 1118 to be retained on the animal's ear. Attachment of the device 1110 to the animal's ear, collection of the blood and removal from the ear is thus substantially the same as for the tenth example.

Figure 27B:
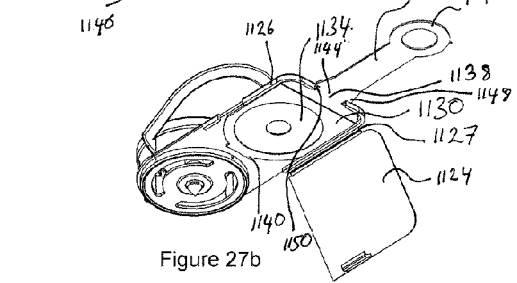
Figure 30:
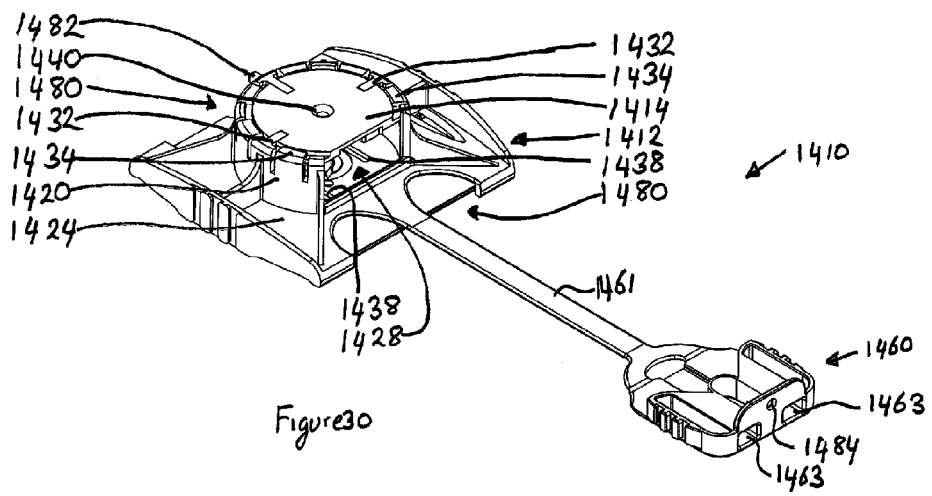
FIG. 30 is a perspective view from above of a fourteenth example of the invention.
Figure 31:
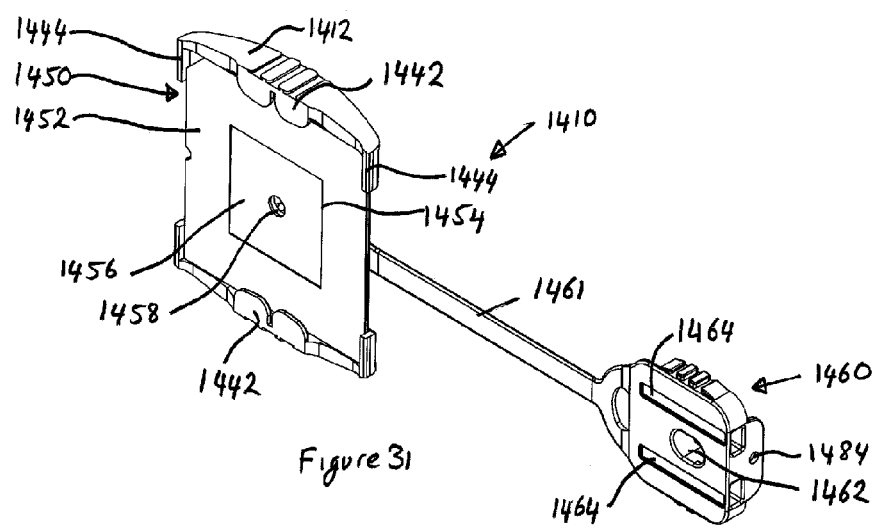
FIG. 31 is a perspective view from below of the fourteenth example.

Once the device 1110 has been removed from the ear the user pulls the carrier sideways relative to the housing 1120 and cartridge 1112. The carrier is preferably a flexible plastics material and the sideways force causes the tab 1146 to deflect and allow the carrier 1130 to move sideways. Alternatively, the tab 1146 may be configured to break off on application of a suitable force. The carrier moves sideways until the locking portion has passed through the opening 1138. As seen in FIG. 27b, the locking portion has angled tabs 1148 that are wider than the opening and a necked region 1150 slightly smaller than the opening. Thus the carrier can be pulled out, with the tabs 1148 deflecting the side walls to pass through the opening 1138. Once the tabs 1148 have passed though the opening the walls return to their normal position and prevent the handle and carrier being pushed back into the housing. In this position the sampling media 1134 is located under the cover 1124.

The entire device may then be sent to a laboratory for further processing. At the laboratory the cover is opened and the carrier removed from the rest of the device for further processing.

If desired the housing may be provided with a line of weakness 1152 in its upper and side walls. After withdrawal of the carrier the housing, with the sampling media 1134 secured within, may be removed from the cartridge by the user bending the outer part of the housing about the line of weakness 1152 to break the upper and side walls at that point. The separated housing may then be sent to a laboratory and the cartridge disposed of.

Example 12

The device 1210 of the twelfth example, shown in FIG. 28, is substantially the same as the eleventh example of FIGS. 25 to 27 and operates substantially the same. However, the device 1210 is provided with an integral press pad 1212 that is attached to the handle 1214 of the cartridge 1216 via strap 1218. The press pad is adapted to locate on the lower jaw of an ear tagging gun, in a similar manner to press pad 814 of the eighth example. The press pad 1212 has an aperture or recess 1220 that, in use, is located opposite the center of the cartridge 1216. However, the aperture is much larger than the pin in the cartridge and does not serve to retain the pin when the pin is driven through the animal's ear. The press pad 1212 is provided so as to avoid any possible contamination of the sample from the ear tagging gun and the aperture is provided to allow the pin to pass through the ear without hindrance from the press pad.

After the device has been attached to the animal's ear, using the steps set out in relation to the eleventh example, the press pad 1212 remains on the lower jaw of the ear tagging gun. The press pad 1212 is removed and the device left on the animal for about 20 to 30 seconds. The user can then remove the device 1210 by grasping the press pad 1212 and pulling the away from the ear.

Example 13

The device 1310 of the thirteenth example, shown in FIGS. 29A to F has a cartridge 1312 and integral press pad 1316 joined together by strap 1314 and loop 1318. The internals of the cartridge 1312 is substantially the same as those of examples eight to twelve. The press pad 1316 is similar to that of the twelfth example and has an aperture 1324 into which the piercing pin of the cartridge extends but does not engage.

Extending across the underside 1332 of the cartridge 1312 is sampling media 1326. The sampling media 1326 is part of a sampling media assembly 1327 that includes a handle 1322 that extends through a hollow housing 1320. Suitable materials for the handle 1322 and housing 1320 include paper, thin cardboard and plastics films or sheets. Preferably the handle 1322 is also a carrier for the sampling media. If desired the handle and sampling media may be formed of the same material The sampling media assembly 1327 extends between two tabs 1328 and the housing extends generally vertically from the upper surface of the tabs 1328. The sampling media assembly 1372 has a T-shaped end 1323 that engages tabs 1325 on the other side of the cartridge (see FIG. 28) and so the sampling media is held in position underneath the cartridge 1312. Preferably the cartridge is configured to maintain the housing generally vertical.

In use the cartridge is mounted on the plunger of an ear tagging gun 1349 and the press pad mounted on the lower jaw 1342, as seen in FIGS. 29 E & F. In this position the strap 1314 is located within the opening of the jaws and the housing extends upwards, leaving the opening to the jaws relatively unimpeded. The device is clamped to an animal's ear as previously described, the press pad is removed from the tagging gun 1340 and the cartridge left on the animal for an appropriate time. As with the twelfth example, the user may remove the device by grasping the press pad 1316 and pulling away from the ear, as shown in FIG. 29D.

After removal from the ear, preferably the housing and sampling media assembly 1327 are removed from the cartridge by disengaging from the tabs 1328 and 1325. The user then grasps the handle 1322 and pulls the sampling media into the housing 1320, where it is protected from contamination. The housing is then sent for further processing, such as in a laboratory, whilst the remainder of the device, namely the cartridge 1312, press pad 1316 and connecting strap 1314 and loop 1318 are disposed of.

If desired, the housing and sampling media may remain on the cartridge before retraction of the sampling media into the housing. If this occurs, preferably the housing is rotated so as to extend generally sideways from the cartridge, as in FIG. 29B before the sampling media is retracted into the housing.

Example 14

The device 1410 of the fourteenth example is shown in FIGS. 30 to 34.

The device 1410 operates similar to that of the eighth to thirteenth examples in having a spring loaded platen 1414 having cutting blades 1418 and central pin 1426. The platen, blades and pin are depressed using ear tagging pliers or a gun, as described later.

Figure 33:
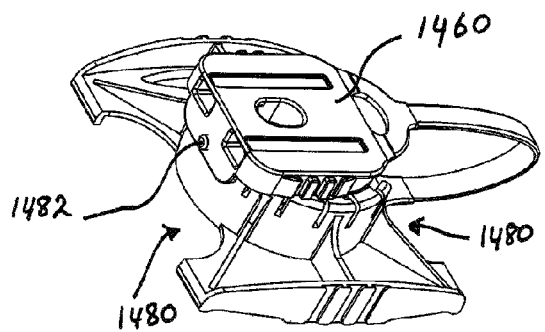
FIG. 33 is a perspective view from above of the fourteenth example after use.
Figure 34:
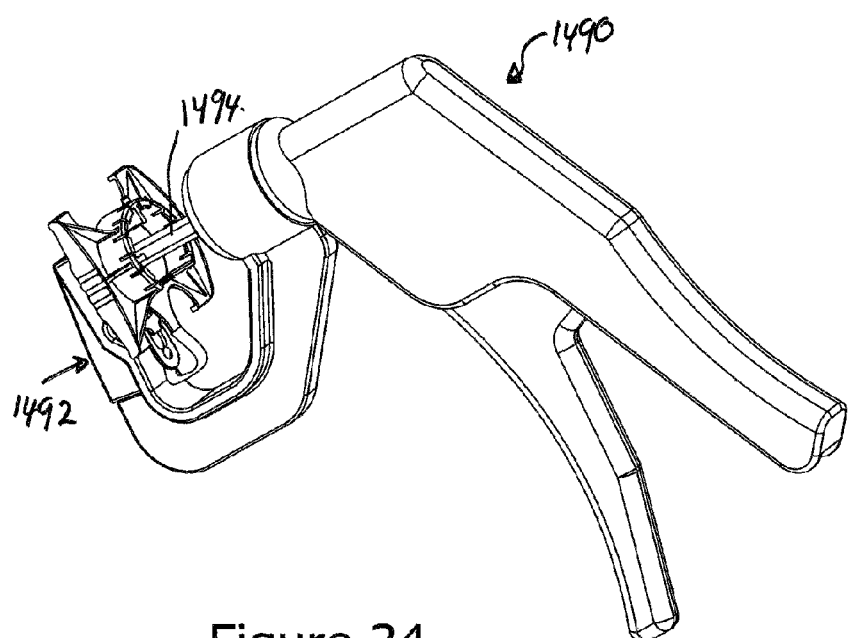
FIG. 34 is a perspective view of the fourteenth example mounted on an ear tagging gun after application to the animal. For clarity the animal's flesh is not shown.

The device 1410 has a housing 1412 and platen 1414 with integral blades 1418 located within the housing. The housing comprises part circular side wall 1420 extending upwards from base 1424 and defines a generally cylindrical space 1428. There is no rear wall, so allowing use with both ear tagging pliers and guns, as shown in FIGS. 33 and 34, respectively. The platen is now round and not rectangular as stated this should be modified.

A spring 1430, located around the pin 1426 and extending between the base 1424 and the underside of the platen 1414, biases the platen away from the base 1424.

The platen 1414 is generally circular and slides vertically within the side wall 1420. The side wall 1420 has inwardly extending vertical ribs 1432 that locate the platen and limit movement to vertical movement.

At the top of side wall 1420 are inwardly extending walls or tabs 1434 that prevent the platen moving out of the housing. These tabs 1434 provide a snap fit for the platen 1414 and allow the platen to be introduced into the cylindrical space 1428 by merely pushing the platen downwards, deflecting the tabs sideways and then allowing the tabs to snap back over the top of the platen. The platen 1414 may have a recessed periphery so the top of the platen and the top of the tabs align.

Located in the base 1424 is aperture 1436 sized to allow pin 1426 to pass through when the platen 1414 is depressed. The pin is similar to that of examples 8 to 13 and has an arrow shaped head 1427.

The base also has linear slots 1438 that align with the blades 1418 and allow the blades to pass through when the platen is depressed.

The upper face of the platen has a recess 1440 for mounting on a press pin 1472 of a set of ear tagging pliers or ear tagging gun.

The underside of the base is recessed to receive sample media carrier 1450.

Side tabs 1442 and end walls 1444 retain the sample media carrier 1450 in the recess. The sample media carrier comprises a carrier 1452 with a rectangular window 1454 with the actual sampling media 1456 mounted on the card over the window 1454. This allows the user to manipulate the card without contacting the actual sampling media 1456. The sampling media preferably has an aperture 1458 that aligns with the pin 1426 and so allows the pin to pass through the media.

The device 1410 also includes a press pad 1460 integrally formed with the housing 1412 and attached thereto by flexible strap 1461.

The press pad 1460 is similar to that of the thirteenth example and has a central aperture 1462 that is oversized to allow the pin 1426 to pass into the aperture but not engage the pin.

Figure 32:
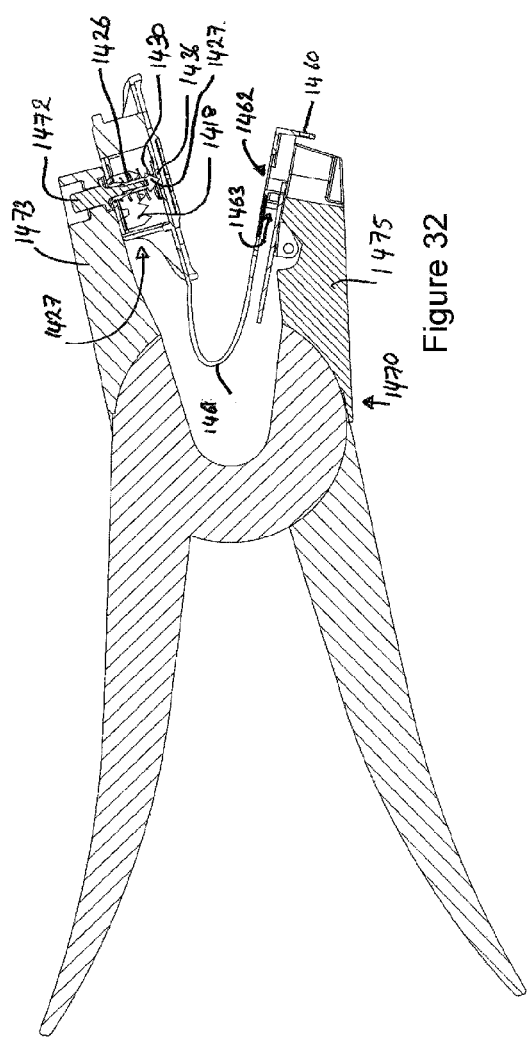
FIG. 32 is a side cross sectional view of a fourteenth example mounted on a pair of ear tag pliers before application to the animal. For clarity the animal's flesh is not shown

Elongate bores 1463 are provided to allow mounting of the press pad 1460 on the lower jaws of ear tagging pliers or gun, as shown in FIGS. 32 and 33. The upper surface of the press pad is also provided with elongate grooves 1464, which, in use, align with the blades 1418. This allows the blades 1418 to pass through a thin ear of an animal and into the grooves, rather than bearing against the upper surface of the press pad. This means that when the pliers are squeezed together all force is transmitted through the ear, so compressing the ear and aiding in release of blood.

In use the platen is mounted on the press pin 1472 of the upper jaw 1473 a pair of ear tagging pliers 1470 and the press pad is mounted on the lower jaws 1475, as shown in FIG. 32. Although the platen is free to rotate on or with the pin 1470 the strap 1461 tends to align the housing with the upper jaw, as shown.

The device is used as previously described with examples 8 to 13. The animal's ear is placed between the jaws and the jaws clamped together, driving the platen downwards. The pin 1426 passes through the apertures 1436 & 1458 in the base 1424 and the sampling media 1456, respectively and into and through the animal's ear. The pin extends into but does not engage recess 1462 The blades 1418 pass through slots 1438 and cut through the sampling media and into the animal's ear.

The upper jaw of the pliers passes into the rectangular aperture 1427, which is why the side wall 1420 is not continuous.

The press pad 1460 provides a surface against which the ear is pressed during this action. The pin 1426 passes through the ear and into the aperture 1462 in the press pad. As mentioned above, the aperture 1462 is oversized and the pin is not retained by the press pad.

The jaws are separated. The spring 1430 withdraws the platen 1414 relative to the housing 1412 and the ear until the arrow shaped head 1427 of the pin 1426 catches on the underside of the ear. Continued separation of the jaws results in separation of the press pin 1472 of the pliers from the platen. The press pad 1460 is not engaged with the pin 1426 and may then be moved with the pliers from the ear for subsequent removal from the lower jaw 1475, leaving the pliers free to receive another device.

As with examples 10 to 13, the spring maintains some pressure on the ear and maintains the sampling media against the skin. After a sufficient period of time the user merely grasps the housing or the press pad and pulls the device from the animal's ear, withdrawing pin 1426 through the animal's ear and allowing the spring 1430 to fully retract the platen, blades and pin.

After use the user may grasp the carrier 1452 via cut outs 1480 and remove the carrier with the sampling media 1456 from the housing.

As seen in FIG. 33, after use the press pad 1460 may be clipped to the top of the housing 1412 to prevent access to the platen. In the example shown the front of the side wall 1420 has a pin 1482 that is received by bore 1484 on press pad 1460. This may be a semi-permanent fixing, so that once attached the press pad cannot be removed, but in the preferred embodiment this is a simple interference fit.

Although the top of the platen 1414 is accessible, this is not critical as it has been found that the blades 1438 need not be sharpened metal or the like that are classified as "sharps" requiring guarding.

As shown in FIG. 34 the device 1410 may be used with an ear tagging gun 1490, with the press pad mounted on the lower jaw 1492 and the housing 1412 on the press pin (not shown) of the plunger 1494. Operation is as previously described with reference to the pliers and earlier examples.

While fourteen examples of devices formed in accordance with the invention have been described and illustrated, along with a number of variants, it will be appreciated that many more examples of devices of the invention are possible and that many more modifications of the examples provided can be made without departing from the scope of the present invention as outlined in the above summary of the invention.

Unless the context clearly requires otherwise, throughout the description and the claims the words 'comprise', 'comprising', and the like are to be construed in an inclusive sense as opposed to an exclusive or exhaustive sense; that is to say, in the sense of "including, but not limited to".

The claims defining the invention are as follows:

1. A device for collecting a blood sample from an animal on sampling media placed next to the animal's flesh, the device comprising:
   a holder for holding the sampling media for placement on the flesh of an animal;
   spike means operable to first pass through the sampling media and to then penetrate into the flesh of the animal to create a puncture site to allow blood emerging from the site to be collected by the sampling media during and/or after penetration of the flesh;
   a retainer for temporarily retaining the device on the animal whilst blood is collected on the sampling media and for allowing the device to be removed from the animal substantially intact for subsequent removal of the sampling media with the blood from the device, and
   a press pad located, in use, to sandwich the flesh between the sampling media and the press pad as the spike means are driven into the flesh,
   wherein, at least a part of the retainer is adapted to be driven into and/or through the animal's flesh to temporarily retain the device on the animal.

2. The device of claim 1 wherein at least a part of the retainer engages in the flesh of the animal and/or sandwiches the flesh between the sampling media and at least part of the retainer.

3. The device of claim 1 wherein, in use, at least a part of the retainer passes through the animal's flesh to engage a rear face of the flesh to temporarily retain the device on the animal.

4. The device of claim 1 wherein the press pad includes an aperture or recess into which at least a part of the retainer may pass when the spike means are driven into the animal's flesh.

5. The device of claim 4 wherein, in use, at least a part of the retainer passes through the animal's flesh and releaseably engages the press pad.

6. The device of claim 5 wherein the retainer includes a pin having a shank and an engagement portion larger than the shank and the aperture or recess has a section of smaller size than the engagement portion, whereby, once the engagement portion has passed the section, it is releaseably retained by the press pad.

7. The device of claim 6 wherein the aperture or recess is an elongate slot, whereby the pin may be disengaged from the press pad by relative moment of the pin along the slot.

8. The device of claim 7 wherein the slot has an end section and adapted to receive the engagement portion, a necked region smaller than the shank located between the end section and the other end and a divergent section that increases in width from the necked region to the other end.

9. The device of claim 1 wherein the press pad includes at least one recess, bore or aperture for mounting on the lower jaw of an ear tagging gun or of a pair of ear tagging pliers.

10. The device of claim 1 wherein the retainer includes a pin having a shank and an engagement portion larger than the shank.

11. The device of claim 1 wherein the said spike means is movable between a first position in which at least said spike means are located to one side of the sampling media and a second position in which at least the said spike means extend through the sampling media into the animal's flesh, the device including a guard for preventing or limiting access to the spike means when in the first position.

12. The device of claim 1 including biasing means that biases the said spike means toward a retracted position.

13. The device of claim 12 wherein, whilst temporarily retained on the animal, the biasing means biases the sampling media against the surface of the flesh.

14. The device of claim 1 wherein the spike means are withdrawn from the site and back through the sampling media during or after collection of the blood.

15. The device of claim 1 including a platen assembly said platen assembly including a platen, said spike means and at least part of said retainer.

16. The device of claim 15 wherein the platen is generally planar and has a first surface, the retainer includes a retainer pin having a head at its free end extending generally from the center of the first surface and said spike means includes blades extending from said first surface on at least opposed sides of the retainer pin.

17. The device of claim 16 wherein the platen assembly includes a recess on a second surface for receiving a press pin of an ear tagging gun or of a pair of ear tagging pliers.

18. The device of claim 1 including a recess and said sampling media is movable between an operative position, in which it is located out of the recess and under the spike means and a storage position, in which is located in the recess remote from the spike means.

19. A device for collecting a blood sample from an animal on sampling media placed next to the animal's flesh, the device comprising:
   a holder for holding the sampling media for placement on the flesh of an animal;
   spike means operable to first pass through the sampling media and to then penetrate into the flesh of the animal to create a puncture site to allow blood emerging from the site to be collected by the sampling media during and/or after penetration of the flesh, and
   a retainer for temporarily retaining the device on the animal whilst blood is collected on the sampling media and for allowing the device to be removed from the animal substantially intact for subsequent removal of the sampling media with the blood from the device,
wherein at least a part of the retainer passes through the flesh of the animal and engages a rear face of the flesh to temporarily retain the device on the animal.

20. The device of claim 19 wherein the retainer includes a pin having a shank and an engagement portion larger than the shank.

21. The device of claim 19 wherein the spike means is withdrawn from the site and back through the sampling media during or after collection of the blood.

22. The device of claim 19 wherein the said spike means is movable between a first position in which at least said spike means are located to one side of the sampling media and a second position in which at least the said spike means extend through the sampling media into the animal's flesh, the device including a guard for preventing or limiting access to the spike means when in the first position.

23. The device of claim 19 including biasing means that biases the said spike means toward a retracted position.

24. The device of claim 22 wherein, whilst temporarily retained on the animal, the biasing means biases the sampling media against the surface of the flesh.

25. The device of claim 19 including a platen assembly said platen assembly including a platen, said spike means and at least part of said retainer.

26. The device of claim 25 wherein the platen is generally planar and has a first surface, the retainer includes a retainer pin having a head at its free end extending generally from the center of the first surface and said spike means includes blades extending from said first surface on at least opposed sides of the retainer pin.

27. The device of claim 26 wherein the platen assembly includes a recess on a second surface for receiving a press pin of an ear tagging gun or of a pair of ear tagging pliers.

28. The device of claim 19 including a recess and said sampling media is movable between an operative position, in which it is located out of the recess and under the spike means and a storage position, in which is located in the recess remote from the spike means.

* * * * *